(12) United States Patent
Chang et al.

(10) Patent No.: US 10,423,819 B2
(45) Date of Patent: Sep. 24, 2019

(54) METHOD AND APPARATUS FOR IMAGE PROCESSING AND VISUALIZATION FOR ANALYZING CELL KINEMATICS IN CELL CULTURE

(71) Applicant: Chung Yuan Christian University, Taoyuan (TW)

(72) Inventors: Yuan-Hsiang Chang, Taoyuan (TW); Hideo Yokota, Saitama (JP); Kuniya Abe, Ibaraki (JP); Ming-Dar Tsai, Taoyuan (TW)

(73) Assignee: Chung Yuan Christian University, Taoyuan (TW)

( * ) Notice: Subject to any disclaimer, the term of this patent is extended or adjusted under 35 U.S.C. 154(b) by 67 days.

(21) Appl. No.: 15/800,047

(22) Filed: Oct. 31, 2017

(65) Prior Publication Data

US 2019/0130161 A1   May 2, 2019

(51) Int. Cl.
| | |
|---|---|
| *G06K 9/00* | (2006.01) |
| *G01N 15/02* | (2006.01) |
| *G06T 7/00* | (2017.01) |
| *G06T 7/207* | (2017.01) |
| *G06T 7/60* | (2017.01) |
| *G06T 7/35* | (2017.01) |

(Continued)

(52) U.S. Cl.
CPC ......... *G06K 9/00127* (2013.01); *G01N 15/02* (2013.01); *G01N 15/1468* (2013.01); *G06T 7/0002* (2013.01); *G06T 7/11* (2017.01); *G06T 7/207* (2017.01); *G06T 7/35* (2017.01); *G06T 7/55* (2017.01); *G06T 7/60* (2013.01); *G01N 2015/0003* (2013.01); *G01N 2015/0065* (2013.01); *G01N 2015/0092* (2013.01); *G01N 2015/025* (2013.01); *G01N 2015/1075* (2013.01); *G01N 2015/1087* (2013.01); *G01N 2015/1093* (2013.01); *G06T 2207/10056* (2013.01); *G06T 2207/30024* (2013.01)

(58) Field of Classification Search
CPC .................................................. G06K 9/00127
See application file for complete search history.

(56) References Cited

U.S. PATENT DOCUMENTS

| | | | |
|---|---|---|---|
| 6,917,884 B2* | 7/2005 | Sammak | G01N 15/1475 |
| | | | 345/626 |
| 7,817,841 B2* | 10/2010 | Padfield | G06K 9/0014 |
| | | | 382/133 |

(Continued)

OTHER PUBLICATIONS

Chang et al. "Fluorescence Microscopy Image Processing and Visualization for Analyzing Cell Kinematics, Proliferation and Attachment in Mouse Embryonic Stem Cell Culture".

(Continued)

*Primary Examiner* — Gandhi Thirugnanam

(57) ABSTRACT

Disclosed herein are methods for analyzing cell kinematics in a nucleated cell culture from a time-series sequence of multiple fluorescence microscopic images of the nucleated cell culture. The method includes the steps of, (a) identifying every cell nucleus in each fluorescence microscopic image; (b) identifying every cell cluster using the cell nuclei identified in the step (a); and (c) tracking the cells and/or cell clusters using the cell nuclei and cell clusters identified for the fluorescence microscopic images in steps (a) and (b) respectively.

24 Claims, 16 Drawing Sheets
(10 of 16 Drawing Sheet(s) Filed in Color)

(51) Int. Cl.
*G06T 7/55* (2017.01)
*G06T 7/11* (2017.01)
*G01N 15/14* (2006.01)
*G01N 15/00* (2006.01)
*G01N 15/10* (2006.01)

(56) References Cited

U.S. PATENT DOCUMENTS

| | | | |
|---|---|---|---|
| 7,957,911 B2* | 6/2011 | Harris | G02B 21/0028 |
| | | | 382/130 |
| 8,588,503 B2* | 11/2013 | Adiga | G06T 7/0012 |
| | | | 382/133 |
| 8,666,119 B1* | 3/2014 | Mallet | G06T 19/00 |
| | | | 382/107 |
| 2005/0002552 A1* | 1/2005 | Dunn | G01N 15/1475 |
| | | | 382/133 |
| 2006/0083418 A1* | 4/2006 | Watson | G06K 9/00127 |
| | | | 382/133 |
| 2006/0127881 A1* | 6/2006 | Wong | G06K 9/00127 |
| | | | 435/4 |
| 2008/0176276 A1* | 7/2008 | Arai | G01N 33/5005 |
| | | | 435/40.5 |
| 2010/0002929 A1* | 1/2010 | Sammak | G06K 9/00127 |
| | | | 382/133 |
| 2010/0046823 A1* | 2/2010 | O Ruanaidh | G06K 9/00134 |
| | | | 382/133 |
| 2010/0080439 A1* | 4/2010 | Karam | G06K 9/00134 |
| | | | 382/133 |
| 2010/0135566 A1* | 6/2010 | Joanidopoulos | G06K 9/0014 |
| | | | 382/133 |
| 2011/0002525 A1* | 1/2011 | Mimura | C12M 23/48 |
| | | | 382/133 |
| 2011/0013821 A1* | 1/2011 | Mimura | G01N 15/1475 |
| | | | 382/133 |
| 2011/0254943 A1* | 10/2011 | Ozinsky | G01N 21/6458 |
| | | | 348/79 |
| 2012/0177611 A1* | 7/2012 | Blau | C12N 5/0068 |
| | | | 424/93.7 |
| 2013/0070054 A1* | 3/2013 | Takaya | G02B 21/0076 |
| | | | 348/46 |
| 2013/0182935 A1* | 7/2013 | Wang | G06K 9/3233 |
| | | | 382/133 |
| 2013/0194410 A1* | 8/2013 | Topman | G06K 9/0014 |
| | | | 348/79 |
| 2014/0247972 A1* | 9/2014 | Wang | G06K 9/6227 |
| | | | 382/133 |
| 2015/0286859 A1* | 10/2015 | Zaytsev | G06F 3/017 |
| | | | 382/103 |
| 2015/0310613 A1* | 10/2015 | Murakami | G02B 21/365 |
| | | | 382/128 |
| 2016/0189377 A1* | 6/2016 | Houjou | G06T 7/11 |
| | | | 382/133 |
| 2018/0232879 A1* | 8/2018 | Chang | G06T 7/0012 |
| 2018/0239949 A1* | 8/2018 | Chander | G01N 33/5011 |

OTHER PUBLICATIONS

Chang et al. "Automated Detection and Tracking of Cell Clusters in Time-Lapse Fluorescence Microscopy Images", Medical and Biological Engineering, Jan. 17, 2017.

Yokota et al. "3D Segmentation, Visualization and Quantitative Analysis of Differentiation Activity for Mouse Embryonic Stem Cells using Time-lapse Fluorescence Microscopy Images".

Qian et al. "A Multi-Threshold Adaptive Filtering for Image Enhancement", Jul. 1990.

* cited by examiner (a)　　　　　　　(b)　　　　　　　(c)

(a)

(b)

METHOD AND APPARATUS FOR IMAGE PROCESSING AND VISUALIZATION FOR ANALYZING CELL KINEMATICS IN CELL CULTURE

STATEMENT REGARDING PRIOR DISCLOSURES BY THE INVENTOR OR A JOINT INVENTOR UNDER 37 C.F.R. 1.77(B)(6)

Part of the subject matter of the invention described in the present application was published by the inventors, Yuan-Hsiang Chang, Hideo Yokota, Kuniya Abe, and Ming-Dar Tsai in an article titled "Detection and Localization of Mouse Induced Pluripotent Stem Cell Formation using Time-Lapse Fluorescence Microscopy Images," which was disclosed during the 2016 IEEE 16th International Conference on BioInformatics and BioEngineering (BIBE) held between Oct. 31 to Nov. 2, 2016. Part of the subject matter of the invention described in the present application was published by the inventors, Yuan-Hsiang Chang, Hideo Yokota, Kuniya Abe, Chia-Tong Tang, and Ming-Dar in an article titled "Automated Detection and Tracking of Cell Clusters in Time-Lapse Fluorescence Microscopy Images," which was first published online by Journal of Medical and Biological Engineering on Jan. 17, 2017. Part of the subject matter of the invention described in the present application was published by the inventors, Hideo Yokota, Kuniya Abe, and Ming-Dar Tsai in an article titled "3D Segmentation, Visualization and Quantitative Analysis of Differentiation Activity for Mouse Embryonic Stem Cells using Time-lapse Fluorescence Microscopy Images," which was disclosed during the 2017 IEEE 17th International Conference on BioInformatics and BioEngineering (BIBE) held between Oct. 23 to 25, 2017. In view of the foregoing, the above-mentioned publications or disclosures were made by and/or originated from all member of the inventive entity of the present invention less than one year before the filing date of the present application. A copy of each article is provided in a concurrently filed Information Disclosure Statement pursuant to the guidance of 78 Fed. Reg. 11076 (Feb. 14, 2013).

BACKGROUND OF THE INVENTION

1. Field of the Invention

The present disclosure relates to the imaging processing of cell kinematics in a nucleated cell culture.

2. Description of Related Art

Fluorescence microscopy has become a powerful and popular tool to obtain digital images from live cells, which help cell biologists visualize and analyze kinematics of cells and/or cell clusters. However, to analyze cell kinematics (such as, cell motion, reproduction, diffusion, and attachment), a massive number of time-series images would be taken, and therefore, the interpretation of these data is quite tedious and time-consuming.

The versatility of fluorescence labeling provides pinpoint specificity and the optical sectioning capability of multidimensional fluorescence has advantages of image multidimensionality. Be that as it may, tracking fluorescent cells faces challenges of non-homogenous staining, low signal-to-noise ratio, uneven background illumination, and photobleaching.

To facilitate the analysis, the fluorescence images are often segmented automatically. Nevertheless, the segmented images are usually of low contrast and poor depth resolutions due to the tight packing of cells. In view of this, various techniques or algorithms have been developed for the automatic segmentation. Although these methods may yield the segmentation of cell nuclei in microscopic images, the detection results are often limited in terms of 3D visualization of cells and/or colonies.

In view of the foregoing, there exists a need in the related art to provide a method capable of efficiently evaluating the positions, velocities, and states of cell clusters in the time-lapse fluorescence microscopy image.

SUMMARY

The following presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

In one aspect, the present disclosure is directed to a method that analyze cell kinematics in a nucleated cell culture. In some embodiments, the present method automatically detects and tracks nucleated cells (such as, embryonic stem cells, induced pluripotent stem cells (iPS cells), somatic cells, and germ cells) and colonies from a time-series sequence of fluorescence microscopic images of the nucleated cell culture. Further, in some embodiments, the present method quantitatively analyzes the kinematics of nucleated cells and colonies from the fluorescence microscopic images.

According to some embodiments of the present disclosure, each fluorescence microscopic image comprises a plurality of subimages taken from different fields and the method comprising the following steps: (a) identifying every cell nucleus in each fluorescence microscopic image; (b) identifying every cell cluster using the cell nuclei identified in the step (a); and (c) tracking the cells and/or cell clusters using the cell nuclei and cell clusters identified for the time series sequence of fluorescence microscopic images in steps (a) and (b) respectively.

In some optional embodiments, the step (a) comprises the steps of, (a1) applying a bilateral filtering to each fluorescence microscopic image; (a2) adjusting the fluorescence illumination of the subimages of the fields across each fluorescence microscopic image that is processed by the step (a1); (a3) detecting every cell nucleus in each fluorescence microscopic image that is processed by the step (a2); (a4) refining the contour of each cell nucleus detected in the step (a3); and (a5) identifying voxels belonging to the same cell nucleus in each fluorescence microscopic image.

According to certain embodiments of the present disclosure, the step (a1) is performed by applying a non-linear filter according to Equation 1:

$$I_p = \frac{1}{W_p} \sum_{q \in S} G_{\sigma_s}(\|p-q\|) \; G_{\sigma_s}(|I_p - I_q|) I_q, \qquad \text{(Equation 1)}$$

where p represents a target pixel in each fluorescence microscopic image, q represents a nearby pixel that is around the target pixel p, $I_p$ represents the color of the target pixel p, $I_q$ represents the color of the nearby pixel q, S represents a set of neighborhood pixels that are around the target pixel p, $G_{\sigma_s}$ represents the standard deviation of a Gaussian filter in which the pixel is weighted according to the distance between the target pixel p and the nearby pixel q, $G_{\sigma_s}$ represents the standard deviation of a Gaussian filter in which the pixel is weighted according to the pixel color differences between the target pixel p and the nearby pixel q, and $W_p$ is determined according to Equation 2:

$$W_p = \sum_{q \in S} G_{\sigma_s}(\|p-q\|) G_{\sigma_s}(|I_p - I_q|). \qquad \text{(Equation 2)}$$

In some optional embodiments, the step (a2) is performed by applying adaptive thresholding according to Equation 3:

$$g(x, y) = \begin{cases} 255 & f_s(x, y) > t(x, y) \\ 0 & \text{otherwise} \end{cases}, \qquad \text{(Equation 3)}$$

where g(x, y) represents the resulting image after the adaptive thresholding, $f_s(x,y)$ represents the resulting image after the step (a1), and t(x, y) is the adaptive threshold that is evaluated locally as the weighted average of the neighborhood pixels in each fluorescence microscopic image.

According to some embodiments, the step (a4) is performed by hole-filling followed by applying a convex hull algorithm.

In some optional embodiments, the step (a5) is performed using 3D connected component labeling to identify a plurality of connected components. In these cases, the present method may further comprise the step of, (a6) assigning a unique identifier (ID) for each cell in the three-dimensional space.

According to some embodiments of the present disclosure, the step (b) is performed by hierarchical clustering. Alternatively, the step (b) comprises the step of assigning a unique identifier for each cell cluster, according to some embodiments of the present disclosure.

In the case where the step (a5) is performed using 3D connected component labeling, the step (b) may comprise the steps of, (b1) determining the geometric centroid for one of the connected components as a cell center; (b2) counting the number n of nearby connected components that are within a radius r with respect to the cell center, and if n≥k, then keeping the cell center; else, discarding the cell center; (b3) giving the remaining connected components a clustering label if they belong to the same cell cluster, wherein the clustering label is unique to the cell cluster; (b4) finding and drawing a bounding rectangle for the cell cluster; and (b5) returning the clustering label and bounding rectangle of the cell cluster.

In the embodiments where the step (b) is performed using steps (b1) to (b5), the step (c) may optionally comprise the steps of, (c1) generating a three-dimensional visualization of the cell cluster by polygonalizing the connected components and rendering the resultant polygons; and (c2) calculating the position and velocity of the cell cluster and each cell inside the cell cluster, and determining the state change of the cell cluster and the cells inside the cell cluster between frames.

According to optional embodiments of the present disclosure, the step (c2) comprises the steps of, determining the geometric centroid for the cell cluster as a cluster center for the clustering label; calculating the number of the clustering labels for each frame; calculating the position p(x,y,z) of the cluster center for each frame; calculating the mean velocity v of the cluster center for each frame; if the number of the clustering labels at frame t+1 is less than the number of the clustering labels at frame t, then merging the clusters, else, keeping track of clusters; and returning the position and mean velocity of the cell cluster.

In another aspect, the present disclosure is directed to a method that analyzes cell kinematics in a nucleated cell culture from a time-series sequence of time-lapse fluorescence microscopic images of the nucleated cell culture.

According to some embodiments of the present disclosure, each fluorescence microscopic image comprises a plurality of subimages taken from different fields and the method comprising the following steps: (a) identifying every cell nucleus in each fluorescence microscopic image by adaptive background subtraction; (b) identifying every cell cluster using the cell nuclei identified in the step (a); and (c) tracking the cells and/or cell clusters using the cell nuclei and cell clusters identified for the time series sequence of fluorescence microscopic images in steps (a) and (b) respectively.

According to some embodiments of the present disclosure, the adaptive background subtraction is performed according to Equation 4:

$$\hat{f}(x,y,t) = |f(x,y,t) - B(x,y,t)| \qquad \text{(Equation 4)},$$

where f(x,y,t) is the current frame and B(x,y,t) is the current background model; and if $\hat{f}(x,y,t) \geq T$, then $(x,y,t) \in F$, else, $(x,y,t) \in B$, where T is a pre-selected threshold, F represents the detected cell clusters, and B represents a background model without any cell clusters.

Alternatively, according to other embodiments of the present disclosure, the step (a), in addition to the adaptive background subtraction, further comprises the steps of, (a1) labelling the regions of cell clusters in the frame, thereby assigning a cluster label for the cell cluster region; and (a2) using an inpainting method to produce a background model for subsequent frames, wherein the background model is according to Equation 5:

$$B(x, y, t) = \qquad \text{(Equation 5)}$$
$$\begin{cases} (1-\alpha) \cdot B(x, y, t-1) + \alpha \cdot f(x, y, t-1) & \text{if } (x, y, t-1) \in \mathcal{B} \\ I(x, y, t-1) & \text{if } (x, y, t-1) \in \mathcal{F} \end{cases},$$

where α is an updating factor in the range of 0 and 1, and I(x,y,t−1) is acquired using the inpainting method in the previous frame.

In embodiments where the step (a) comprises the steps (a1) and (a2) in the preceding paragraph, the step (c) optionally comprises the step of, (c1) determining the geometric centroid for the cell cluster as a cluster center.

In some optional embodiments, the step (c) further comprises the step of, (c2) applying a Discrete Kalman filter for the cluster in the frame according to Equation 6:

$$x_k = A\, x_{k-1} + B\, u_k + w_k$$

$$z_k = H_k x_k + v_k \qquad \text{(Equation 6)},$$

where $X_{k-1}$ and $X_k$ represent the state vectors at time k−1 and k, respectively, the matrix A is a state transition matrix, the matrix B is a control-input matrix, $u_k$ is the control vector, $w_k$ is the process noise, $z_k$ is the measurement vector, $H_k$ is the observation transition model, and $v_k$ is the process noise, wherein $w_k$ has the Gaussian distribution with the covariance matrix $Q_k$ and $v_k$ has the Gaussian distribution with the covariance matrix $R_k$.

In optional embodiments, the step (c) further comprises the steps of, (c3) tracking the cluster center of the cell cluster, wherein the plurality of fluorescence microscopic images are two-dimensional (2D) images or three-dimensional (3D) images, and the state vector $X_k$ is a 4-dimensional vector [x,y,dx/dt,dy/dt] for the 2D images or a 6-dimensional vector [x,y,z, dx/dt,dy/dt, dz/dt] for the 3D images, in which the x, y, z values represent the coordinates of the cluster center, the dx/dt, dy/dt, dz/dt values represent the moving velocity of the cluster center, and the transition matrix is according to Equation 7 for 2D images or Equation 8 for 3D images, $$A = \begin{bmatrix} 1 & 0 & 1 & 0 \\ 0 & 1 & 0 & 1 \\ 0 & 0 & 1 & 0 \\ 0 & 0 & 0 & 1 \end{bmatrix} \quad \text{(Equation 7)}$$

$$A = \begin{bmatrix} 1 & 0 & 0 & 1 & 0 & 0 \\ 0 & 1 & 0 & 0 & 1 & 0 \\ 0 & 0 & 1 & 0 & 0 & 1 \\ 0 & 0 & 0 & 1 & 0 & 0 \\ 0 & 0 & 0 & 0 & 1 & 0 \\ 0 & 0 & 0 & 0 & 0 & 1 \end{bmatrix} \quad \text{(Equation 8);}$$

and (c4) updating the state of the cell cluster according to Equation 9 and Equation 10:

$$x_k = x_k^- + K_k(z_k^- - H_k^-) \quad \text{(Equation 9),}$$

$$P_k = (1 - K_k H_k) P_k^- \quad \text{(Equation 10),}$$

where $z_k$ is selected by the closest coordinate of the cell cluster, $P_k^-$ represents the error covariance, which is an a-prior estimate for the covariance at time k, and is obtained by Equation 11:

$$P_k^- = A P_{k-1} A^T + Q_{k-1} \quad \text{(Equation 11),}$$

where $P_{k-1}$ represents the error covariance at time k−1 and $Q_{k-1}$ represents the covariance matrix of the process noise, $K_k$ is the Kalman gain and is obtained by Equation 12:

$$K_k = P_k^- H_k^T (H_k P_k^- H_k^T + R_k)^{-1} \quad \text{(Equation 12).}$$

In some optional embodiments, the step (c) further comprises the step of determining the state of the cluster at the next frame into one of the following states:
(1) a moving state: if the cluster center of a predicted cell cluster is located inside the detected cell cluster region as defined by Equation 13, then assigning the previous cluster label to the detected cell cluster region:

if $x_k \in R_k^l$, then State=Moving  (Equation 13), where $R_k^l$ represents the detected cell cluster region after the background subtraction in the k-th frame, where l=1 . . . n is the assigned label for the cell cluster region, and the location of the cell cluster is defined as $x_k^l$ with the cluster label l in the k-th frame;
(2) an appearance state: if the detected cell cluster region is new and do not overlap with any existing cluster region as defined by Equation 14, then assigning a new cluster label to the detected cell cluster region and initializing a Discrete Kalman filter according to Equation 6:

if $R_k \cap R_{k-1}^l = \phi$, $\forall l=1 \ldots, n_{k-1}$, then
State=Appearance  (Equation 14);

(3) a disappearance state: if the predicted cluster center is not located inside any existing cluster regions for consecutive $\hat{k}$ frames as defined by Equation 15, then removing the cluster label of the predicted cluster:

if $x_{k-\hat{k}} \notin R_{k-\hat{k}}^l$, $\forall l=1 \ldots, n_{k-\hat{k}}$, the
State=Disppearance  (Equation 15);

(4) a merging state: if two or more predicted cluster centers are located inside an existing cluster region as defined by Equation 16, then keeping the cluster label of the existing cluster region:

if $x_k \in R_k^l$ and $x_k \in R_{k'}^l$, k≠k', then State=Merging  (Equation 16);

(5) a splitting state: if a detected region is a new region that partially overlaps with any existing cluster regions as defined by Equation 17, then assigning a new cluster label to the detected region and initializing a Discrete Kalman filter according to Equation 6:

if $R_k^{l_1} \cap R_{k-1}^l \neq \phi$ and $R_k^{l_2} \cap R_{k-1}^l \neq \phi$, $l_1 \neq l_2$, then
State=Splitting  (Equation 17);

In yet another aspect, the present disclosure is directed to a method that analyzes cell kinematics in a nucleated cell culture from a time-series sequence of time-lapse fluorescence microscopic images of the nucleated cell culture wherein the time-lapse fluorescence microscopic images comprise a plurality of cytoplasm images and a plurality of nucleus images, and each cytoplasm image has a corresponding nucleus image taken at the same time.

According to some embodiments of the present disclosure, each fluorescence microscopic image comprises a plurality of subimages taken from different fields and the method comprising the following steps: (a) identifying every cell nucleus in each fluorescence microscopic image by a bilateral filtering; (b) identifying every cell cluster using the cell nuclei identified in the step (a); and (c) tracking the cells and/or cell clusters using the cell nuclei and cell clusters identified for the time series sequence of fluorescence microscopic images in steps (a) and (b) respectively.

In some optional embodiments, the bilateral filtering used in the steps (a1) and (a3) is a nonlinear filter defined by Equation 18 below, $$g(i,j) = \frac{\sum_{k,l} f(k,l) w(i,j,k,l)}{\sum_{k,l} w(i,j,k,l)}, \quad \text{(Equation 18),}$$

where, $$w(i,j,k,l) = \exp\left(-\frac{(i-k)^2 + (j-l)^2}{2\sigma_d^2} - \frac{\|f(i,j) - f(k,l)\|^2}{2\sigma_r^2}\right). \quad \text{(Equation 19)}$$

Still optionally, the step (b) comprises the step of, (b1) identifying voxels belonging to the same cell nucleus in each nucleus image using 3D connected component labeling to identify a plurality of connected components; (b2) assigning a unique identifier (ID) for each cell in the three-dimensional space; (b3) determining the geometric centroid for one of the connected component as a cell center; (b4) counting the number n of nearby connected components that are within a radius r with respect to the cell center, and if n≥k, then keeping the cell center; else, discarding the cell center; (b5) giving the remaining connected components a clustering label if they belong to the same cell cluster, wherein the clustering label is unique to each cell cluster; (b6) finding and drawing a bounding rectangle for the cell cluster; and (b7) returning the clustering label and bounding rectangle of the cell cluster.

In some optional embodiments, the step (c) comprises the step of, (c1) obtaining time-series 3D images of cell nuclei and cytoplasm by volume rendering the cytoplasm images and the nucleus images, wherein at each time step, two consecutive cytoplasm images and two consecutive corresponding nucleus images are rendered simultaneously.

According to some other embodiments of the present disclosure, the step (c) further comprises the step of, (c2) determining the geometric centroid for the cell cluster or the nucleus as a 3D center; and (c3) calculating the velocity of the cell cluster or the nucleus based on the displacement between the 3D centers of adjacent time-steps.

In some further optional embodiments, the method further comprises the step of, (d) computing a ratio of the cytoplasm surface area to the volume (S/V ratio) of the cell.

In still another aspect, the present disclosure is directed to a tangible computer-readable storage medium encoded with computer-readable instructions (a computer program or software) that when executed by a programmable device (a processor or a computer) cause the programmable device to perform the present methods for analyzing cell kinematics in a nucleated cell culture from a time-series sequence of fluorescence microscopic images of the nucleated cell culture. All or various aspects/embodiments of the methods according to the invention that are described herein can be executed by these encoded instructions when run in the programmable device.

In still yet another aspect, the present invention is directed to a system for analyzing cell kinematics in a nucleated cell culture from a time-series sequence of fluorescence microscopic images of the nucleated cell culture.

According to certain embodiments, the system comprises, an apparatus configured to obtain the fluorescence microscopic images and a control unit that comprises a processor and a memory for storing a plurality of instructions which, when executed by the processor, causing the processor to perform the present method. All or various aspects/embodiments of the methods according to the invention that are described herein can be executed by the processor.

Many of the attendant features and advantages of the present disclosure will becomes better understood with reference to the following detailed description considered in connection with the accompanying drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The present description will be better understood from the following detailed description read in light of the accompanying drawings, where.

DESCRIPTION

Figure 1A:
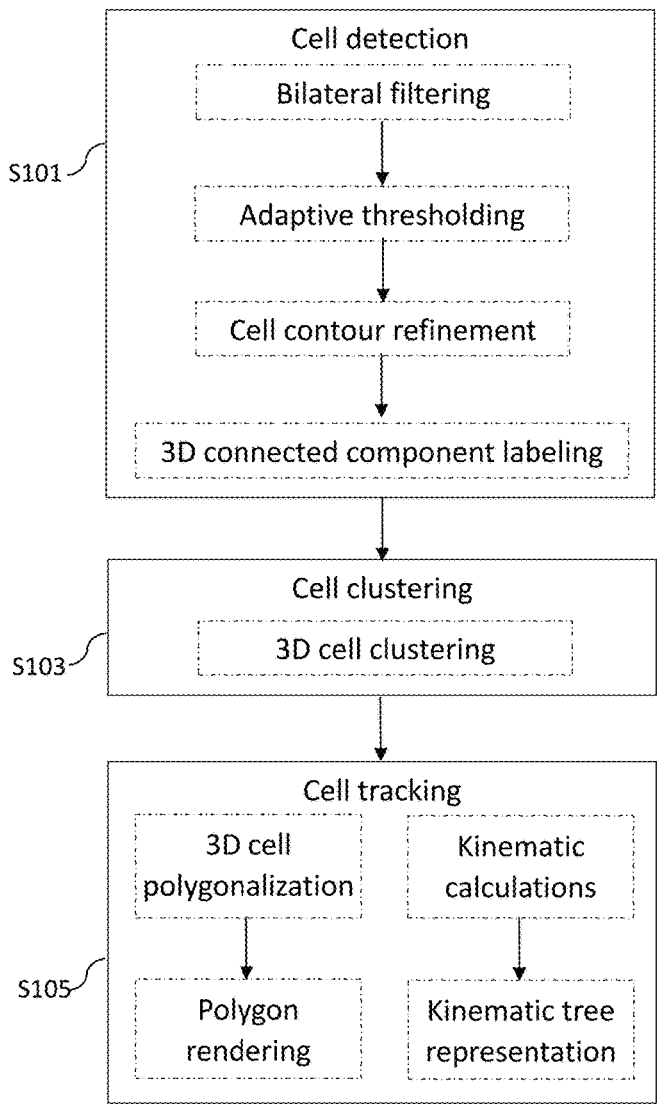
FIG. 1A is a flow diagram illustrating method steps for performing the methods for analyzing cell kinematics in a nucleated cell culture from a time-series sequence of fluorescence microscopic images of the nucleated cell culture according to embodiments of the present disclosure.

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

For convenience, certain terms employed in the specification, examples and appended claims are collected here. Unless otherwise defined herein, scientific and technical terminologies employed in the present disclosure shall have the meanings that are commonly understood and used by one of ordinary skill in the art.

Unless otherwise required by context, it will be understood that singular terms shall include plural forms of the same and plural terms shall include the singular. Also, as used herein and in the claims, the terms "at least one" and "one or more" have the same meaning and include one, two, three, or more. Furthermore, the phrases "at least one of A, B, and C", "at least one of A, B, or C" and "at least one of A, B and/or C," as use throughout this specification and the appended claims, are intended to cover A alone, B alone, C alone, A and B together, B and C together, A and C together, as well as A, B, and C together.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about." Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques. Ranges can be expressed herein as from one endpoint to another endpoint or between two endpoints. All ranges disclosed herein are inclusive of the endpoints, unless specified otherwise.

As used therein, the term "nucleated cell" refers to any cell containing a nucleus therein. Examples of nucleated cells include, but are not limited to, embryonic stem cells, stem cells, pluripotent cells, induced pluripotent stem (iPS) cells, somatic cells and germ cells. By the term "nucleus" is meant a membrane-enclosed organelle found in eukaryotic cells that contains most of the cell's genetic material organized in the form of chromosomes.

Fluorescence imaging of live cells is a powerful tool for the study of dynamic cellular processes and events, such as embryogenesis and cell differentiation. With the advancement of the imaging technology, fluorescence imaging is capable of yielding high spatial and temporal resolution.

In view of the foregoing, the first aspect of the present disclosure is directed to a method for analyzing cell kinematics in a nucleated cell culture from a time-series sequence of fluorescence microscopic images of the nucleated cell culture. FIG. 1A is a flow chart illustrating a method 100 according to embodiments of the present disclosure.

According to FIG. 1A, the fluorescence microscopic images are first subjected to a cell detection step S101, which aims to identify each and every cell nucleus in each fluorescence microscopic image. Generally, the cell detection step S101 comprises procedures of bilateral filtering, adaptive thresholding, cell contour refinement, and 3D connected component labeling, which are discussed in detail below First, the bilateral filtering is applied to each step to reduce the image noise and improve the signal-to-noise ratio of the image. In this way, the cell contours representing the cell nuclei could be preserved and enhanced. The bilateral filtering is a nonlinear filter and can be defined as:

$$I_p = \frac{1}{W_p} \sum_{q \in S} G_{\sigma_s}(\|p - q\|) G_{\sigma_r}(|I_p - I_q|) I_q, \quad \text{(Equation 1)}$$

where p represents a target pixel in each fluorescence microscopic image, q represents a nearby pixel that is around the target pixel p, $I_p$ represents the color of the target pixel p, $I_q$ represents the color of the nearby pixel q, S represents a set of neighborhood pixels that are around the target pixel p, $G_{\sigma_s}$ represents the standard deviation of a Gaussian filter in which the pixel is weighted according to the distance between the target pixel p and the nearby pixel q, $G_{\sigma_r}$ represents the standard deviation of a Gaussian filter in which the pixel is weighted according to the pixel color differences between the target pixel p and the nearby pixel q, and $W_p$ is determined according to Equation 2:

$$W_p = \sum_{q \in S} G_{\sigma_s}(\|p - q\|) G_{\sigma_r}(|I_p - I_q|). \quad \text{(Equation 2)}$$

For many fluorescence microscopic applications, subimages taken from different fields are often assembled into one image for each time interval. In one example, an image consists of a total of 16 fields, each field contains 512×512 pixels. In these cases, the fluorescence illumination in each field may differ from one another, thereby resulting in non-uniform image characteristics. To address the illumination issue, the adaptive thresholding as defined below is applied, $$g(x, y) = \begin{cases} 255 & f_s(x, y) > t(x, y) \\ 0 & \text{otherwise} \end{cases}, \quad \text{(Equation 3)}$$

where g(x, y) represents the resulting image after the adaptive thresholding, $f_s(x,y)$ represents the resulting image after the step (a1), and t(x, y) is the adaptive threshold that is evaluated locally as the weighted average of the neighborhood pixels in each fluorescence microscopic image.

To refine the shapes of detected regions, it is assumed that the nucleus of the nucleated cell should be present in a local region with a circular or oval shape. Accordingly, a hole-filling technique is first applied, followed by a convex hull algorithm, so that each cell is represented by a closed region with a well-defined circular or oval contour in the fluorescence microscopy images.

The objective of the cell detection step S101 is to automatically identify individual cells and assign a unique ID for each cell in the three-dimensional space. The technique of 3D connected component labeling based on 6-connectivity is applied iteratively so that voxels belonging to the same nucleus can be identified in 3D. Finally, the results of connected components, i.e., 3D closed regions for cell nuclei, are color coded for visualization.

After the cell detection step S101, the present method 100 proceeds to the cell clustering step S103, in which a unique ID is assigned for each cell cluster (colony). In contrast to cluster analysis techniques involving the k parameters (such as k-means, k-nearest neighbor) that require the parameter k to be determined prior to the clustering analysis; the present method incorporates the technique of hierarchical clustering, which is a connectivity based clustering technique. Specifically, the cell clustering step S103 uses the 3D cell clustering algorithm as follows:

(1) For each connected component (CC), determining the geometric centroid for each CC as a cell center;

(2) For each cell center, opening a circular region with a radius r, and counting the number n of nearby CCs that are within the radius r, and if n≥k, then keeping the cell center; else, discarding the cell center;

(3) For the remaining CCs, giving a unique clustering label if they belong to the same cell cluster, wherein the clustering label is unique to each cell cluster;

(4) For each cluster, finding and drawing a bounding rectangle; and (5) Returning the clustering label and bounding rectangle of each cell cluster.

Nest, the present method proceeds to the cell tracking step S105, which includes procedures of visualization, tracking, as well as position, velocity and state representation.

To visualize the connected labeled 3D voxels, a volume processing software, Volume Computer Aided Testing (VCAT, available at http://logistics.riken.jp/vcat) is used. Specifically, the VCAT visualizes, applies meshing, and analyzes a multi-material segmented (labeled) multi-dimensional (2D-4D) image. VCAT polygonalizes the detected cells (i.e., the connected labeled 3D voxels) using a 3D interface, and then renders the polygons. In this way, the user (e.g., a cell biologist) may select a desired perspective to observe the 3D cells in each and every colony.

After the visualization step, a discrete Kalman filter is applied, and an identifier (ID) is assigned to each cell or cluster. Then, the positions, velocities of every cell cluster and cells within the cluster, as well as the state changes of the clusters and cells between frames are calculated. Specifically, the present method uses a tree structure to represent the position, velocity and state changes among the cell clusters (colonies). The algorithm for computing velocities and state changes and represents them in a tree is described as follows:

(1) For each Clustering Labels (CL), determining the geometric centroid for each CL as the clustering center;

(2) For each Frame (F), counting the number of Clustering Labels (NC), computing the position p(x, y, z) of each cluster center; and calculating the mean velocity v of each cluster center;

(3) if the number of clusters at t+1 is less than the number of clusters at t, then merging the clusters, else, keeping track of clusters; and (4) returning clusters' position & clusters' mean velocity.

According to various embodiments of the present disclosure, the state changes include appearance, disappearance, merging (cell cluster attachment), and splitting (cell proliferation).

The present method 100 automatically detects and tracks nucleated cells and colonies, and then quantitatively analyzes the kinematics of nucleated cells and colonies from confocal (3D) time-series fluorescence microscopy images. The reconstructed cell and colonies can be visualized through a 3D interface; meanwhile, kinematics (positions and velocities of cells and colonies) and cell proliferation, and colony attachment are quantitatively analyzed and represented illustratively through a state tree. Using this method, the kinematics, and proliferation of each cell in the nucleated cell colony as well as the kinematics and attachment of the nucleated colonies themselves in the nucleated cell culture could be sought. The present method is particularly useful for studies focusing on the basic features of nucleated cells, such as cell proliferation and differentiation, and gives insight into metastable state of the mammalian stem cells.

Figure 1B:
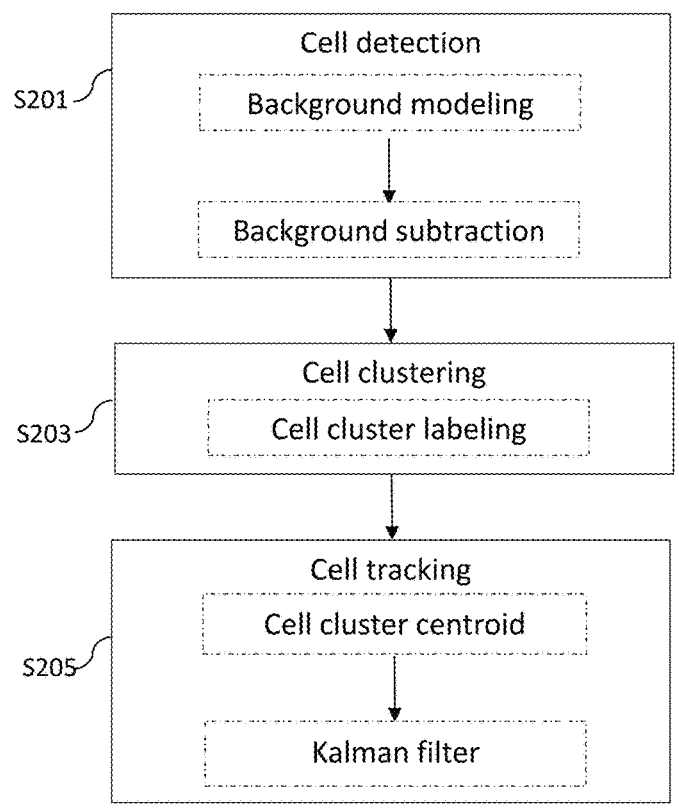
FIG. 1B is a flow diagram illustrating method steps for performing the methods for analyzing cell kinematics in a nucleated cell culture from a time-series sequence of time-lapse fluorescence microscopic images of the nucleated cell culture according to embodiments of the present disclosure.

Furthermore, the second aspect of the present disclosure is directed to a method for analyzing cell kinematics in a nucleated cell culture from a time-series sequence of time-lapse fluorescence microscopic images of the nucleated cell culture. FIG. 1B is a flow chart illustrating a method 200 according to embodiments of the present disclosure.

Generally, the method 200 also comprises three steps, i.e., a cell detection step S201, a cell clustering step S203, and a cell tracking step S205.

Traditionally, frame differencing is used to detect moving objects from time-lapse images, and although this method is straightforward, the results often contain edges associated with the moving cell clusters only. An alternative solution is background subtraction; yet it is sensitive to illumination changes in the video sequences, especially the fluorescence microcopy imaging of live cells.

In view of the foregoing, in the present cell detection step S201, an adaptive background subtraction is adopted to yield accurate segmentation of cells and/or cell clusters. Specifically, a background model is first generated by manually labeling the regions of cell clusters in the first frame of the video sequence, followed by video inpainting to produce the background model for subsequent frames. The adaptive background model as follows is applied according to Equation 5:

$$B(x, y, t) = \begin{cases} (1-\alpha) \cdot B(x, y, t-1) + \alpha \cdot f(x, y, t-1) & \text{if } (x, y, t-1) \in \mathcal{B} \\ I(x, y, t-1) & \text{if } (x, y, t-1) \in \mathcal{F} \end{cases}$$

(Equation 5)

where $\alpha$ is an updating factor in the range of 0 and 1, and $I(x,y,t-1)$ is acquired using the inpainting method in the previous frame.

As a result, the background model is updated in the subsequent frames and the missing pixels in foreground regions are propagated using the neighboring pixels in the background regions. This adaptive background subtraction-based method is capable of detecting cell clusters in time-lapse fluorescence microscopic images even when the images are of low signal-to-noise ratio and uneven background illumination.

Thereafter, in the cell clustering step S203, the 3D connected component labeling technique is used to label cell clusters. For example, the cell clustering step S203 may adopts the 3D cell clustering algorithm described above in the cell clustering step S103.

Next, the method 200 proceeds to the cell tracking step S205, in which the Discrete Kalman filter (DKF) is used for cell cluster tracking. DKF predicts a process's state and uses measurements to correct the predictions. First, the centroid of each cell cluster is computed as the geometric centroid of all the pixels in the cell cluster. For each cell cluster in the first frame, a Kalman filter is created accordingly to track the centroid of the moving cell cluster.

The Kalman filter is defined as:

$$x_k = A\, x_{k-1} + B\, u_k + w_k$$

$$z_k = H_k x_k + v_k \quad \text{(Equation 6)},$$

where $X_{k-1}$ and $X_k$ represent the state vectors at time k−1 and k, respectively, the matrix A is a state transition matrix, the matrix B is a control-input matrix, $u_k$ is the control vector, $w_k$ is the process noise, $z_k$ is the measurement vector, $H_k$ is the observation transition model, and $v_k$ is the process noise, wherein $w_k$ has the Gaussian distribution with the covariance matrix $Q_k$ and $v_k$ has the Gaussian distribution with the covariance matrix $R_k$.

In order to keep track of the location of the cell clusters in time-lapse fluorescence microscopic images, the state $X_k$ is a 4-dimensional vector [x, y, dx/dt, dy/dt] for 2D time-series images and a 6-dimensional vector [x, y, z, dx/dt, dy/dt, dz/dt] for 3D time-series images. Here, the x, y, z values represent the coordinates of the observed cell centroid and the dx/dt, dy/dt, dz/dt values represent its moving velocity in each dimension. In practice, the state transition matrix can thus be defined by Equation 7 (for 2D time-series images) or Equation 8 (for 3D time-series images):

$$A = \begin{bmatrix} 1 & 0 & 1 & 0 \\ 0 & 1 & 0 & 1 \\ 0 & 0 & 1 & 0 \\ 0 & 0 & 0 & 1 \end{bmatrix}, \quad \text{(Equation 7)}$$

$$A = \begin{bmatrix} 1 & 0 & 0 & 1 & 0 & 0 \\ 0 & 1 & 0 & 0 & 1 & 0 \\ 0 & 0 & 1 & 0 & 0 & 1 \\ 0 & 0 & 0 & 1 & 0 & 0 \\ 0 & 0 & 0 & 0 & 1 & 0 \\ 0 & 0 & 0 & 0 & 0 & 1 \end{bmatrix}. \quad \text{(Equation 8)};$$

Using $P_k^-$ to denote the error covariance, the a-prior estimate for the covariance at time k is obtained from the value at time k−1 by Equation 11:

$$P_k^- = AP_{k-1}A^T + Q_{k-1} \quad \text{(Equation 11)},$$

where $P_{k-1}$ represents the error covariance at time k−1 and $Q_{k-1}$ represents the covariance matrix of the process noise, $K_k$ is the Kalman gain and is obtained by Equation 12:

$$K_k = P_k^- H_k^T (H_k P_k^- H_k^T + R_k)^{-1} \quad \text{(Equation 12)},$$

which allows us to update the state by Equation 9 and Equation 10:

$$x_k = x_k^- + K_k(z_k^- - H_k^-) \quad \text{(Equation 9)},$$

$$P_k = (1 - K_k H_k) P_k^- \quad \text{(Equation 10)},$$

where $z_k$ is selected by the closest coordinate of the cell cluster.

To quantitatively evaluate the interactions among every cell cluster over time (i.e., among frames), a cell cluster tracking algorithm is applied. In this algorithm, the detected cell cluster region after the adaptive background subtraction is defined as $R_k^l$ in the k-th frame, where l (l=1 ... n) is the assigned label for the cell cluster region. In addition, the location of the cell cluster is defined as $x_k^l$ with the cluster label l in the k-th frame. The cell cluster tracking algorithm can be described as follows. At the first frame, the cluster numbers, centers, labels and regions are computed and assigned as described in the previous paragraphs. Then, at every successive frame, the state at the next frame of each cluster is computed into one of the following cases (moving, appearance, disappearance, merging, and splitting).

(1) Moving: If the centroid of a predicted cell cluster is located inside the detected cell cluster region as defined by:

$$\text{if } x_k \in R_k^l, \text{ then State=Moving} \quad \text{(Equation 13)},$$

This case indicates the cell cluster is just moving. The previous cluster label is assigned to the detected cell cluster region.

(b) Appearance: If the detected region is new and do not overlap with any existing cluster region as defined by:

$$\text{if } R_k \cap R_{k-1}^l = \phi,\ \forall l=1 \ldots, n_{k-1}, \text{ then State=Appearance} \quad \text{(Equation 14)}.$$

This case indicates a new appearing cell cluster region. A new label is assigned and a Kalman filter is initialized for this cluster.

(c) Disappearance: If the predicted cluster center is not located inside any existing cluster regions for consecutive $\hat{k}$ frames as defined by:

$$\text{if } x_{k-\hat{k}} \notin R_{k-\hat{k}}^l,\ \forall l=1 \ldots, n_{k-\hat{k}}, \text{ the State=Disppearance} \quad \text{(Equation 15)}.$$

This case indicates a cluster disappeared and its label is removed.

(d) Merging: If two or more predicted cluster centers are located inside an existing cluster region as defined by:

$$\text{if } x_k \in R_k^l \text{ and } x_{k'} \in R_k^l,\ k \neq k', \text{ then State=Merging} \quad \text{(Equation 16)}.$$

This case indicates two or more clustered have been merged with the same label.

(e) Splitting: If a detected region is a new region that partially overlaps with any existing cluster regions as defined by:

$$\text{if } R_k^{l_1} \cap R_{k-1}^l \neq \phi \text{ and } R_k^{l_2} \cap R_{k-1}^l \neq \phi,\ l_1 \neq l_2, \text{ then State=Splitting} \quad \text{(Equation 17)}.$$

This case indicates the detected region is new and assigned a label and a Kalman filter.

As could be appreciated, the present method 200 provides a state-of-art motion-based tracking method that repeatedly predicates the position and velocity of every cell cluster in the next frame to determine the optimal position and velocity thereof. The states, such as appearance, disappearance, merging and splitting of cell clusters are computed by the cluster centroid and region information. This method tracks only the centroid but not all the pixels of a cluster so that the computing efficiency can be optimized. Moreover, it is feasible to apply the centroid computation to a three-dimensional setting, which would be very useful in light of the increasing use of 3D time-series images.

Figure 2:
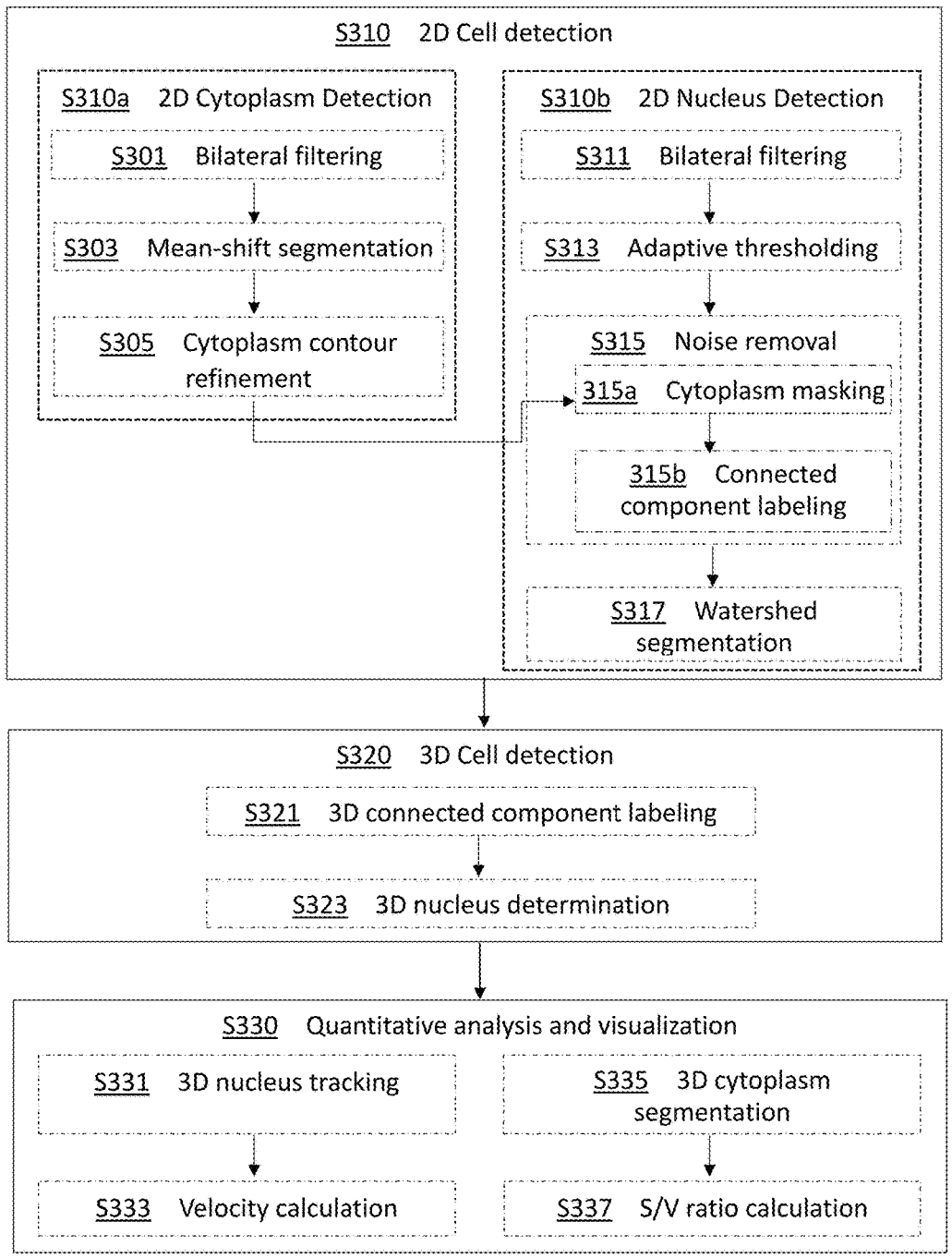
FIG. 2 is a flow diagram illustrating method steps for performing the methods for visualization and/or analyzing differentiation activity in a nucleated cell culture from a time-series sequence of time-lapse fluorescence microscopic images of the nucleated cell culture according to embodiments of the present disclosure.

The third aspect of the present disclosure is directed to a method for analyzing cell kinematics in a nucleated cell culture from a time-series sequence of time-lapse fluorescence microscopic images of the nucleated cell culture; in particular, the time-lapse fluorescence microscopic images comprise a plurality of cytoplasm images and a plurality of nucleus images, and each cytoplasm image has a corresponding nucleus image taken at the same time. FIG. 2 is a flow chart illustrating a method 300 according to embodiments of the present disclosure.

Generally, the method 300 comprises three main steps, i.e., a 2D cell detection step S310, a 3D cell detection step S320, and a quantitative analysis and visualization cell step S330.

In step S310, the cytoplasm image and corresponding nucleus image are first processed separately, and then the processed cytoplasm image and nucleus image are processed collectively.

Specifically, in a 2D cytoplasm detection step S310a, a bilateral filtering is implemented to process the cytoplasm images (step S301). Meanwhile, in a 2D nucleus detection step S310b, the bilateral filtering is also applied to the nucleus images (step S311). As could be appreciated, the two bilateral filtering steps (S301 and S311) may be carried out at the same time or sequentially, and the present invention is not limited to any sequence in which these two steps are performed. The bilateral filtering steps (S301 and S311) intends to remove noises while at the same time preserve boundaries in the microscopy images. According to some embodiments, the bilateral filtering step uses a nonlinear filter defined as Equation 18 below:

$$g(i, j) = \frac{\sum_{k,l} f(k, l) w(i, j, k, l)}{\sum_{k,l} w(i, j, k, l)}, \quad \text{(Equation 18)}$$

where, $$w(i, j, k, l) = \exp\left(-\frac{(i-k)^2 + (j-l)^2}{2\sigma_d^2} - \frac{\|f(i, j) - f(k, l)\|^2}{2\sigma_r^2}\right). \quad \text{(Equation 19)}$$

For each pixel, the value g of the output pixel is computed as a weighted combination of the value f of the input pixel, where $\sigma_d$ and $\sigma_r$ are the smoothing parameters to control the spatial and color distances, respectively. The distance is computed as the norm of the RGB vector differences as Equation 20 below:

$$\|f_1 - f_2\| = \sqrt{(R_1 - R_2)^2 + (G_1 - G_2)^2 + (B_1 - B_2)^2} \quad \text{(Equation 20)}.$$

Returning to the 2D cytoplasm detection step S310a, the cytoplasm image as-processed by the step S301 is then subjected to mean-shift segmentation (step S303) to address the issue of the uneven illumination across the cytoplasm image. According to some embodiments of the present disclosure, the mean-shift segmentation step S3030 is carried out as follows:

(1) Find a histogram for the gray-levels of the cytoplasm image;
(2) Find a local maximum in the histogram;
(3) Replace the value of a pixel using the local maximum; that is, find the nearest local maximum in the neighborhood for each pixel and replace the pixel's value using the local maximum; and
(4) Use the minimum local maximum as the adaptive threshold to produce a corresponding binary image of the cytoplasm image.

Then, in step S305, a contour refinement step is performed on the cytoplasm image as-processed by the step S303. In particular, an OR operation between the nucleus image as-processed by the step S311 and the corresponding cytoplasm image as-processed by the step S303 is implemented to obtain complete cytoplasm shapes based on the assumption that the nucleus locates inside the cytoplasm. As could be appreciated, this step S305 not only refines the contour of the cytoplasm, but also solves the problem of vague boundaries due to the low fluorescence intensity in some of the cytoplasm.

On the other hand, in the 2D nucleus detection step S310b, the nucleus image as-processed by the step S311 is subjected to adaptive thresholding (step S313) to preserve nucleus boundaries while at the same time make the background noises clear (see, J. Qian, K. B. Yu and R. M. Haralick, "A Multi-Threshold Adaptive Filtering for Image Enhancement," IEEE International Conf. Acoustics, Speech, and Signal Processing (ICASSP), vol. 11, 1986, pp. 2467-2470).

Then, the method proceeds to the noise removal step S315, in which the cytoplasm image as-processed by the step S305 is used as a mask to process the corresponding nucleus image as-processed by the step S313 (step S315a), so as to extract the nucleus areas and thus remove the background noises based on the assumption that the nucleus locates inside the cytoplasm.

The noise removal step S315 also includes the application of a connected component labeling algorithm to the nucleus image as-processed by the step S315a (step S315b) to label each nucleus area in the nucleus image and remove small noise-like areas. In this way, the nucleus areas are well preserved, while irrelevant information such as image background noses were removed.

After the noise removal step S315, the as-processed nucleus image is subjected to a watershed segmentation step S317. In this step, small holes inside the nucleus areas are removed using a watershed segmentation algorithm, in which the nucleus image is treated as a geological watershed to separates adjacent nuclei. A convex hull algorithm is then implemented to refine the contour of each nucleus.

After identifying the cell nuclei in the 2D cell detection step S310, the method 300 proceeds to the 3D cell detection step S320, in which cell clusters are detected.

First, in the 3D connected component labeling step S321, 3D connected component labeling based on 6-connectivity is used to identify which nucleus a segmented voxel belongs (being labeled) to. In particular, voxels belonging to the same cell nucleus in each nucleus image using 3D connected component labeling to identify a plurality of connected components. According to various embodiments of the present disclosure, the 3D connected component labeling method is the same as those described above in connection with other aspect/embodiments of the present disclosure.

After labeling, the method 300 proceeds to a 3D nucleus determination step S323, in which each nucleus is represented by a separate set of 3D connected voxels with a unique identifier (or cell ID).

According to some embodiments of the present disclosure, the step S320 also comprises the step of cell clustering in which neighboring nuclei are clustered as a cell colony. According to various embodiments of the present disclosure, the cell clustering comprises the steps as follows. First, a unique identifier (ID) is assigned for each cell in the three-dimensional space. Then, determine the geometric centroid for one of the connected component and the geometric centroid is used as a cell center. Next, the number n of nearby connected components that are within a radius r with respect to the cell center is counted, and if n≥k, then the cell center is kept; else, the cell center is discard. Then, the remaining connected components are given a clustering label if they belong to the same cell cluster, wherein the clustering label is unique to each cell cluster. Next, a bounding rectangle for the cell cluster is found and drawn. Then, the clustering label and bounding rectangle of the cell cluster are returned.

Then, in the quantitative analysis and visualization step S330, the cell nucleus or the cell cluster identified in the step S320 is used for further analysis.

According to some embodiments, 3D images are computed by volume rendering the processed cytoplasm images and nucleus images. In particular, at each time step, two (cytoplasm and nucleus) 3D volumes constituted by two sets of 2D consecutive confocal images are rendered simultaneously. The segmented nucleus voxels in the nucleus volume that is constituted by consecutive confocal nucleus images are assigned as transparent red. The segmented cytoplasm voxels in the cytoplasm volume constituted by consecutive confocal cytoplasm images are assigned as transparent green. The transparency and color are the same for all segmented nucleus voxels. Meanwhile, the transparency of the segmented cytoplasm voxels with low fluorescence response are higher than the ones with high fluorescence response.

Moreover, in the 3D nucleus tracking step S331, a video tracking technique is applied to track each nucleus or cell colony with the time-series 3D volumes constituted by the time-lapse confocal images. The tracking technique is implemented by matching the centroids of 3D nucleus and nucleus colonies with shortest Euclidean distances in adjacent time-series volumes. Then, in the velocity calculation step S333, the velocity of a nucleus or a colony is calculated by dividing the displacement of the 3D centroids of a nuclei or colonies of adjacent time-steps with the time interval.

In addition to the velocity of the moving nucleus or cell cluster, it is also feasible to calculate the ratio of cytoplasm surface area to volume (S/V ratio) of the cell to investigate the shape changes of the cell. To this end, in the 3D cytoplasm segmentation step S335, every cytoplasm voxel (i.e., the voxel that is a cytoplasm voxel but not a nucleus voxel) is processed as follows.

(1) Calculate the distances of said cytoplasm voxel to neighboring 3D nuclei and label said cytoplasm voxel as belonging to the nearest nucleus.
(2) Accumulate the volume of the cytoplasm voxel to the 3D nucleus.
(3) Check if each of the 6 faces of the cytoplasm voxel is a boundary face (the face-neighboring voxel is not a cytoplasm voxel). The area of the face is accumulated to the 3D nucleus After processing all cytoplasm voxels, in the step S337, the surface area and volume of cytoplasm belonging to every 3D nucleus are obtained to calculate the cytoplasm S/V ratio of the 3D nucleus (or the stem cell) according to Equation 21 below, $$S/V \text{ ratio} = \frac{\text{Surface Area}}{\text{Volume}}. \quad \text{(Equation 21)}$$

As could be appreciated, the present method 300 provides an automate method for 3D segmentation, visualization and quantitative analysis of the nucleated cells using time-lapse confocal fluorescence microscopy images. In particular, the present method 300 simultaneously processes two set of images, one from the cytoplasm and the other from the nuclei. The nucleus images are used to segment 2D and then 3D nuclei, and help the cytoplasm segmentation; on the other hand, the cytoplasm images are also used to help the nucleus segmentation. Further, the present method 300 uses a video tracking technique to track and thus calculate velocities of the 3D nuclei, and uses cytoplasm images to calculate the cytoplasm surface and volume of every nucleus. In this way, nucleated cells with different differentiation activity can be visualized and quantitatively analyzed.

According to certain embodiments of the present disclosure, the present methods can be implemented as a computer product that is developed using the Open Source Computer Vision (OpenCV) library.

The subject matter described herein could be implemented using a non-transitory, tangible processor-readable storage medium having stored thereon processor-readable instructions that, when executed by the processor of a programmable device, control the programmable device to perform a method according to embodiments of the present disclosure. Exemplary processor-readable storage media suitable for implementing the subject matter described herein include, but are not limited to, RAM, ROM, EPROM, EEPROM, flash memory or other solid-state memory technology, CD-ROM, DVD, or other optical storage, magnetic cassettes, magnetic tape, magnetic disk storage or other magnetic storage devices, and any other medium which can be used to store the desired information and which can be accessed by the processor. In addition, a processor-readable storage medium that implements the subject matter described herein may be located on a single device or computing platform or may be distributed across multiple devices or computing platforms.

In another aspect of the subject matter described herein, a system for analyzing cell kinematics in a nucleated cell culture from a time-series sequence of fluorescence microscopic images or time-lapse fluorescence microscopic images of the nucleated cell culture is provided. The system comprises an apparatus (hereinafter, a fluorescent image-capturing apparatus) configured to obtain a fluorescence microscopic image of one or more cells and a control unit. The fluorescent image-capturing apparatus is, for example, any suitable fluorescence microscope. The control unit is communicatively connected with the fluorescent image-capturing apparatus and is configured to process the fluorescence microscopic images captured by the apparatus. In particular, the control unit comprises a processor and a memory for storing a plurality of instructions which, when executed by the processor, causing the processor to the present method(s).

The communication between the fluorescent image-capturing apparatus and the control unit may be embodied using various techniques. For example, the system may comprise a network interface to permit communications between the fluorescent image-capturing apparatus and the control unit over a network (such as a local area network (LAN), a wide area network (WAN), the Internet, or a wireless network). In another example, the system may have a system bus that connects various system components including the fluorescent image-capturing apparatus to the control unit. In yet another embodiment, the system may have an output device for the fluorescent image-capturing apparatus to output the data representing the fluorescence microscopic image(s), and an input device for inputting these data into the control unit.

The following Examples are provided to elucidate certain aspects of the present invention and to aid those of skilled in the art in practicing this invention. These Examples are in no way to be considered to limit the scope of the invention in any manner. Without further elaboration, it is believed that one skilled in the art can, based on the description herein, utilize the present invention to its fullest extent.

EXAMPLE 1

(1) Embryonic Stem (ES) Cell Formation

Embryonic stem cells were derived from blastocyst stage embryos obtained from the transgenic mouse strain carrying Mvh-Venus reporter gene. The mES cell line was routinely cultured under feeder-free condition using Glasgow-minimal essential medium (G-MEM; Sigma-Aldrich) supplemented with 14% KSR, 1% ESC culture-grade FBS (Life Technologies), 1 mM sodium pyruvate (Nacalai Tesque), 1 mM nonessential amino acids, 0.1 mM 2-mercaptoethanol, 0.25× penicillin/streptomycin mix, 1,000 U/ml of LIF (ES-GRO; Millipore), 3 µM CHIR99021 (Cayman chemicals), and 1 µM PD0325901 (Wako Pure Chemicals) at 37° C., 5% $CO_2$. pPGK-H2B-mCherry-puro, in which human histone H2B gene was fused to mCherry gene driven by the PGK promoter, was introduced by lipofection into the mES line described above. The ES cells carrying the reporter plasmid were selected by puromycin and the mCherry-expressing cells were further purified by fluorescent activated cell sorting (FACS).

(2) Imaging Conditions

In this study, the CV-1000 (Yokogawa) confocal microscope was used to obtain fluorescence microscopic images of embryonic stem cells. The camera being used is the model Olympus UPLSApo60xO. Table 1 summarizes the microscope setting. Three channels of fluorescent microscopic images of embryonic stem cells were obtained simultaneously. An example set of fluorescence microscopic images of embryonic stem cells were taken at time interval of 20 minutes with a total of 48 frames. Each image (2048×2048 pixels) includes 16 subimages (512×512 pixels) with 0.26 µm pixel widths. The image stack of each time interval includes 12 slices with 2 µm slice interval.

TABLE 1

| Channel Name | Channel 1 | Channel 2 | Channel 3 |
|---|---|---|---|
| Excitation | 405 nm | 488 nm | 561 nm |
| Emission | BP447/60 | BP525/50 | BP617/73 |
| Fluorescent | Hoechst | EGFP | mRFP |
| Exposure | 100 ms | 15 ms | 15 ms |
| Gain | 20% | 60% | 40% |
| Z Slices | 12 | 12 | 12 |

Figure 3:
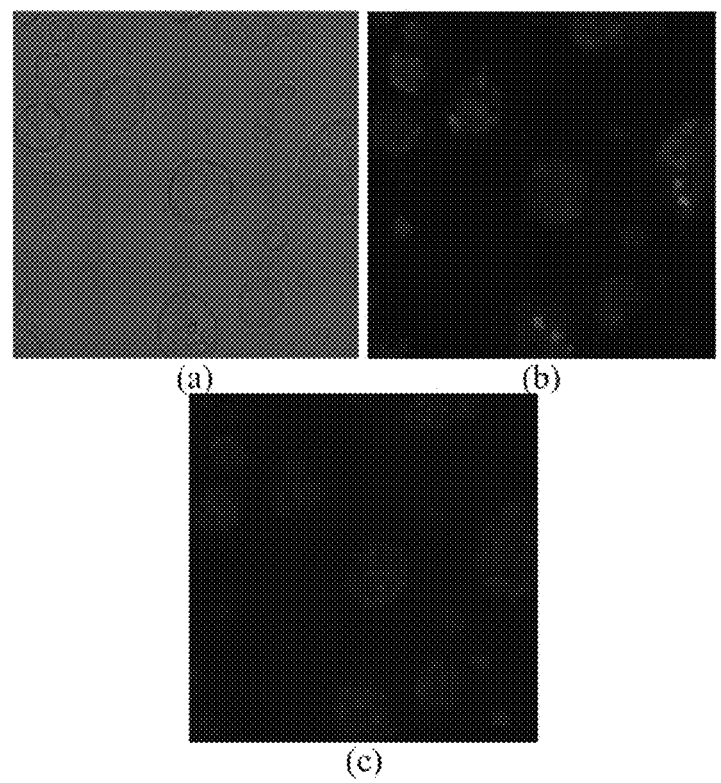
FIG. 3 is a fluorescence microscopic image of embryonic stem cell according to one working example of the present disclosure.

FIG. 3 shows representative fluorescence microscopic images of embryonic stem cells. Panel (a) of FIG. 3 is the gray-level image taken in Channel 1, which is the brightness channel (gray-level image). Panel (b) of FIG. 3 is the image taken in Channel 2, which reveals the cytoplasmic labeling with the Venus (green) fluorescence protein; while panel (c) is taken in Channel 3, which reveals nuclei labeling by mRFP (monomeric red fluorescent protein). Each image (2048×2048 pixels) includes 16 subimages (512×512 pixels) with a fine pixel width of 0.26 µm pixel widths.

(3) Image Processing

The images in this example were processed by our system implementing the method 100 described above. This system was developed using C/C++ programming and the Open Source Computer Vision (OpenCV) library Version 3.0. With a PC equipped with Intel® Core i5 and 8G RAM and the Windows 8 Operating system, it takes less than 2 seconds for the detection of mES stem cell nucleus boundaries in a fluorescence microscopic image.

Figure 4:
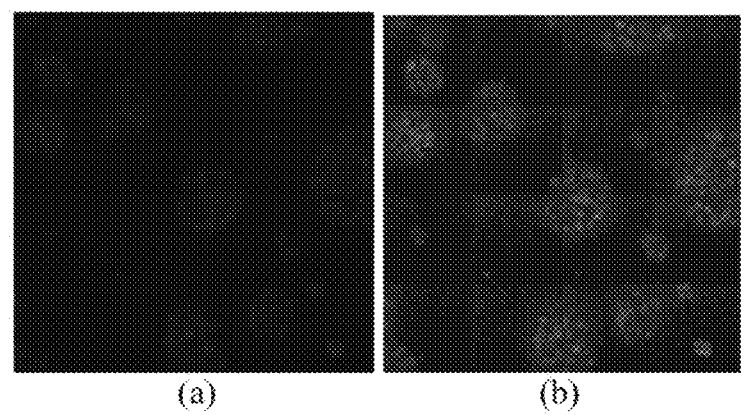
FIG. 4 is an example of the result of the bilateral filtering for image enhancement according to one working example of the present disclosure.

In this example, the fluorescent image from panel (c) of FIG. 3 was first processed by the bilateral filtering of cell detection step S101, as described above, and the results were shown in FIG. 4, in which panel (a) is the original image, whereas panel (b) shows the result after bilateral filtering for image enhancement. The radius of the bilateral filtering was chosen as approximately the radius of an embryonic cell nucleus. By comparing panels (a) and (b) of FIG. 4, it is observed that the contours representing cell nuclei were preserved while a certain degree of image noise has been eliminated.

As discussed above, the image of each field contains 512×512 pixels, and a total of 16 fields (subimages) were collected and assembled for each time interval. As a result, variability of fluorescence illumination is generally observed in different fields, resulting in non-uniform image characteristics (see, for example, panel (b) of FIG. 4). To address the illumination issue, the adaptive thresholding as described in the cell detection step S101 was applied to the image (see, panel (a) of FIG. 5).

Figure 5:
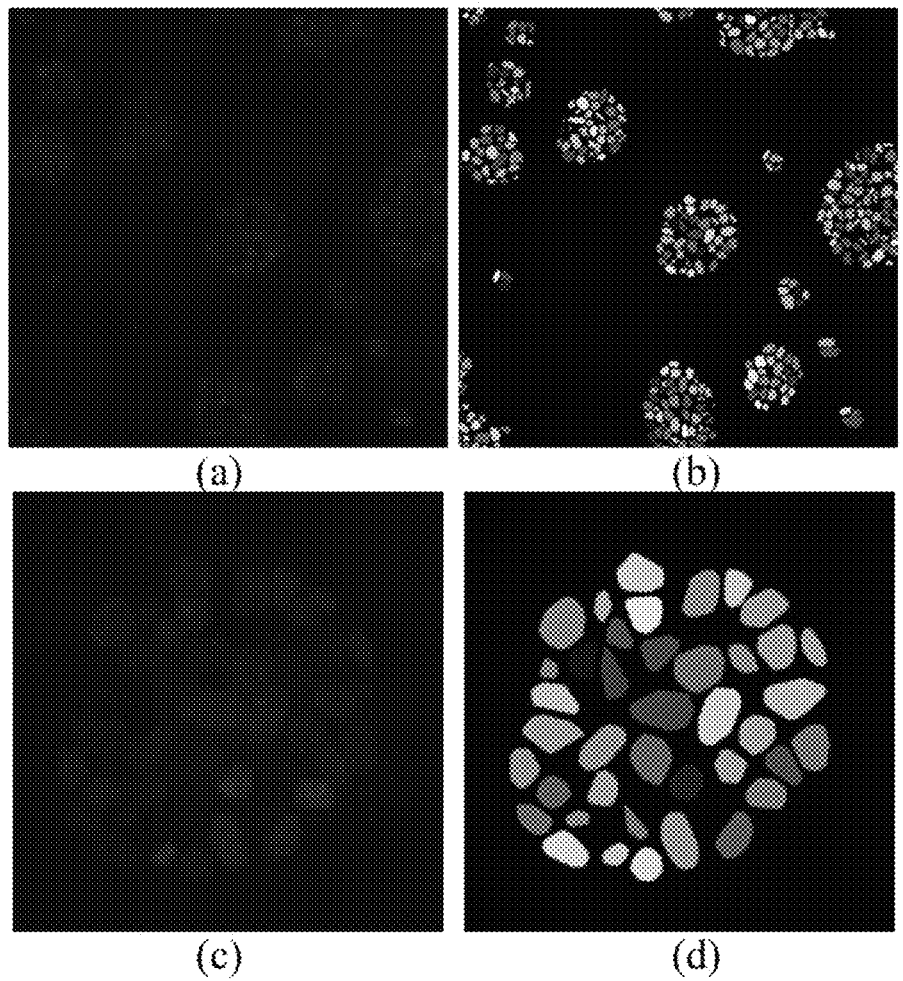
FIG. 5 is an example of the result of the cell detection using the fluorescence microscopic image from FIG. 3.

Thereafter, the 3D connected component labeling was performed so that each individual cell is color-coded for visualization. FIG. 5 shows an example of the cell detection in the fluorescence microscopic image, (a) Original image; (b) Cell detection results for (b); (c) Original image of a cell cluster in the center of (a); (d) Cell detection results for (c). As could be seen in FIG. 5, the criteria of closed regions with circular or oval shapes representing cell nuclei was satisfied using the present method.

Using the fluorescence microscopy images with 373 mES cells manually identified, the performance of our automated method for the segmentation of cell nuclei was evaluated and compared with the conventional watershed algorithm. The results summarized in Table 2 below indicated that the present method 100 achieved a much higher sensitivity in detecting the cell number, as compared with the conventional watershed algorithm did, despite the fact that the original images were of low image contrast and signal-to-noise ratio.

TABLE 2

|  | Watershed algorithm | The present method 100 |
|---|---|---|
| Number of cell nuclei (manually identified) | 373 | 373 |
| Detected number of cell nuclei (manually identified) | 251 | 360 |
| Sensitivity (%) | 67.3 | 96.5 |

The images, after being processed by the cell detection step S101, were subjected to the cell clustering step S103, followed by the cell tracking step S105.

Figure 6:
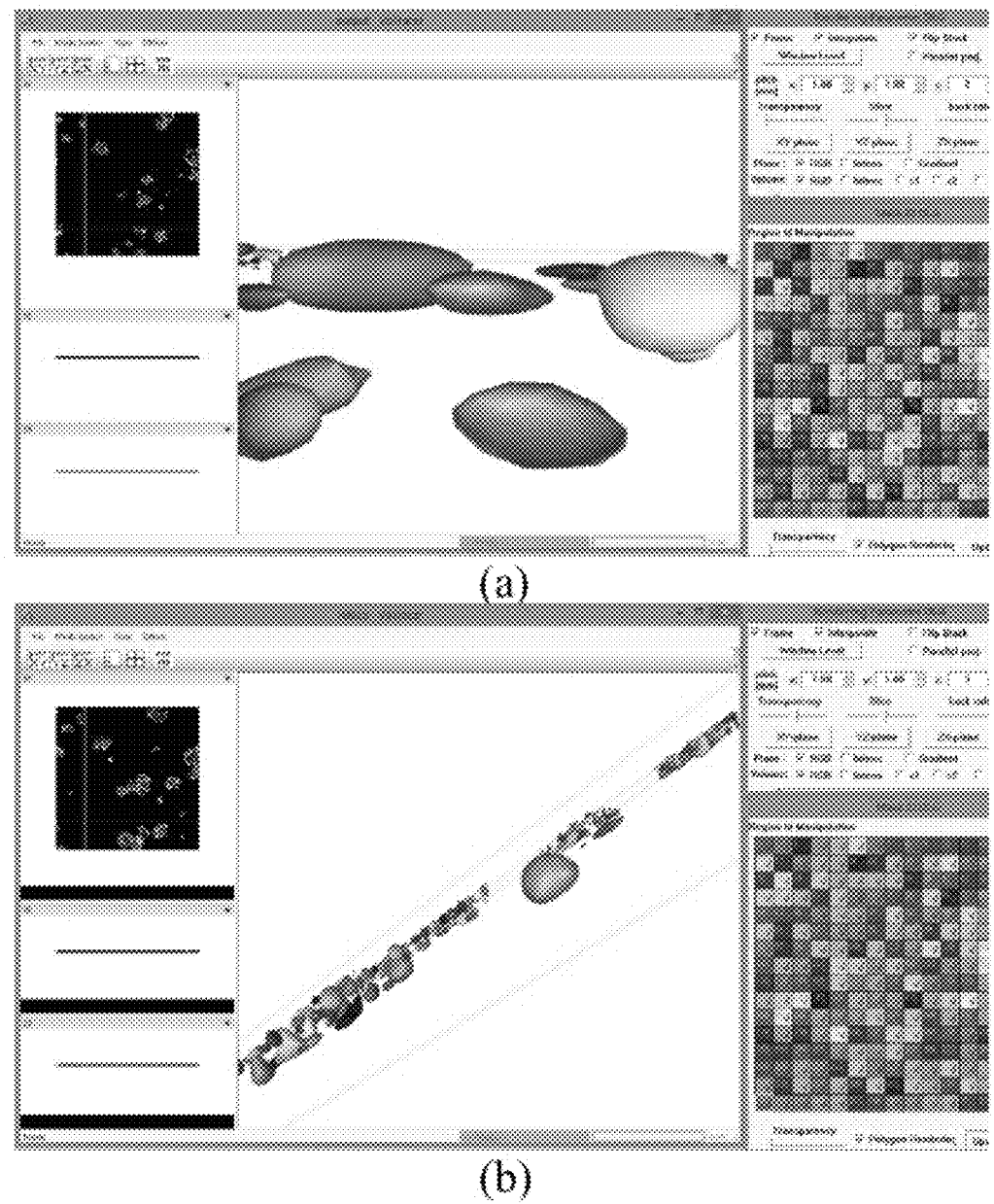
FIG. 6 is an example of the result of the cell and colony visualization by VCAT.

FIG. 6 shows an example of cell and colony visualization by our VCAT algorithm, in which panel (a) is the zoom-in image for observing individual cells in a colony, and (b) is the zoom-out image for observing cells in separate colonies.

Figure 7:
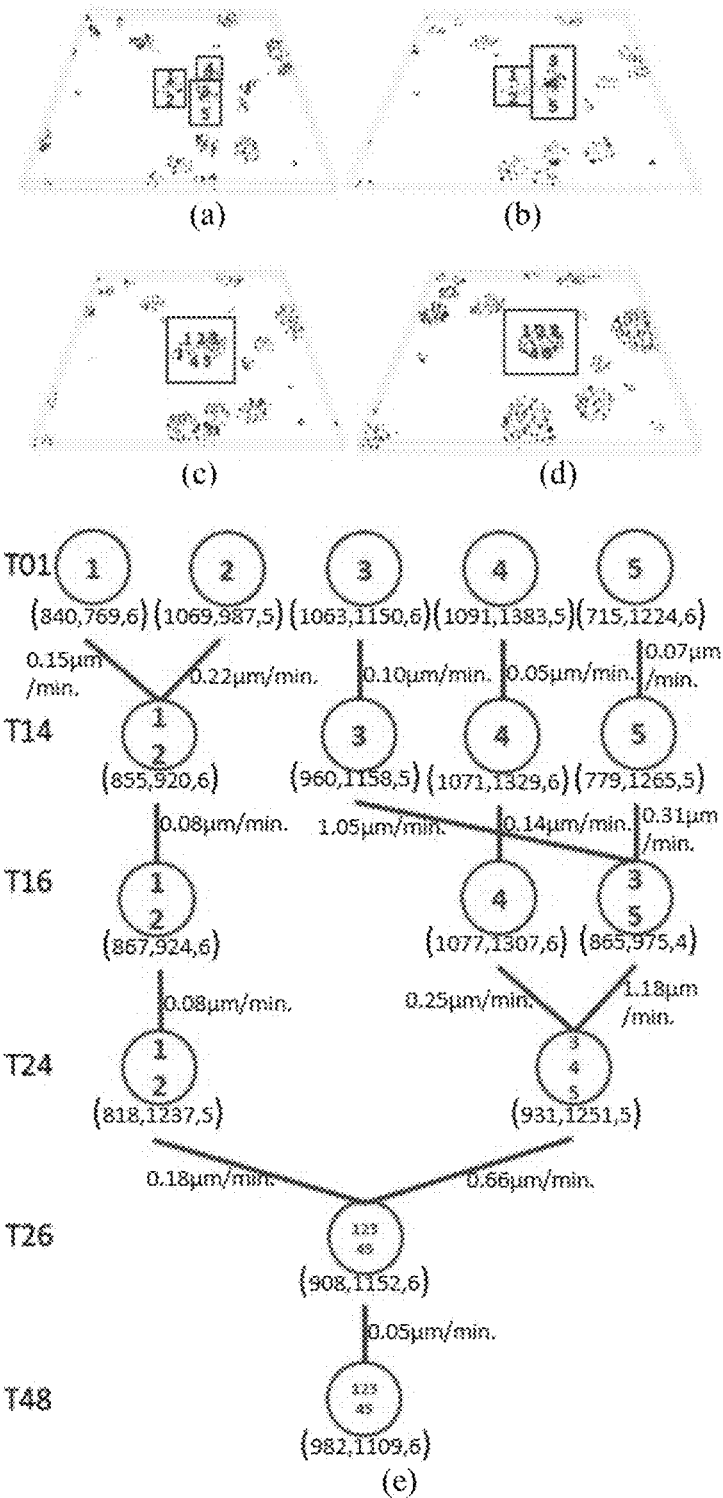
FIG. 7 is an example of the present automated system for the visualization of the kinematics and attachment process of cell clusters according to one working example.

FIG. 7 presents an example result in which the kinematics of the attachment process of some colonies were visualized through our 3D interface and illustrated by the state tree. In particular, panels (a) to (d) are perspective views of the embryonic stem cell clusters, while panel (e) shows a tree structure recording the quantitative analysis results (cluster IDs, positions, and velocities) of five clusters detected and tracked during the colony attachment process through the 48 (T01~T48) time-steps.

As shown in panel (e) of FIG. 7, the five colonies eventually merged into one. The colony 1 & 2 were beginning to merge at the 14$^{th}$ time step with relatively faster velocities, i.e., 0.15 μm and 0.22 μm per minute, respectively.

Figure 8:
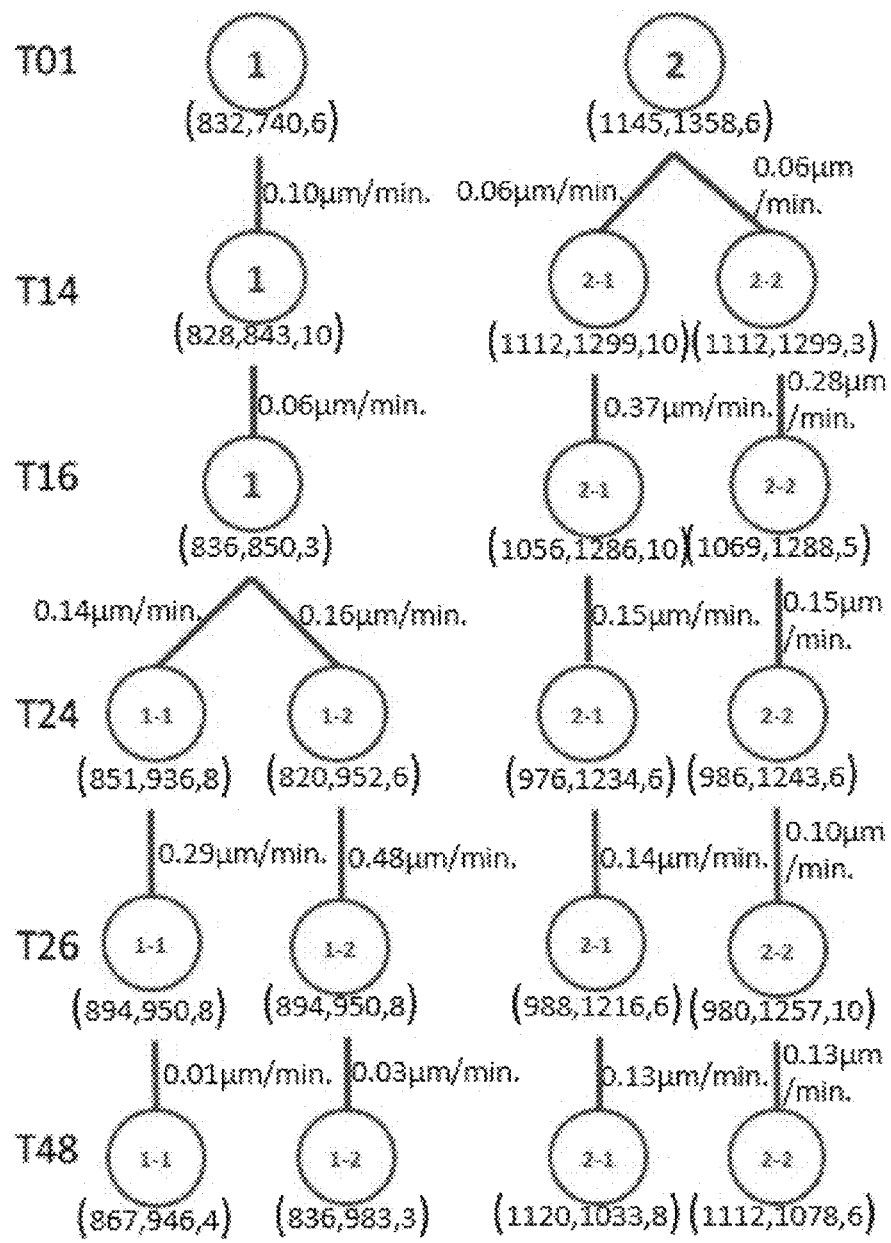
FIG. 8 is a tree structure that records the quantitative analysis results (cell IDs, positions, and velocities) to illustrate the cell kinematics proliferation process according to one working example.

FIG. 8 shows an example illustrating the result of the kinematics and the proliferation process of original two cells in some colony shown in FIG. 7. The cell kinematics and the proliferation process can also be visualized by the 3D interface and the state tree as shown in FIG. 8. Together with the labeled cells and colonies in the 3D images, the state trees provide an easy way to understand the cell colony kinematics and attachment and the cell kinematics and proliferation in a timely manner.

EXAMPLE 2

(1) Embryonic Stem (ES) Cell Formation

The mouse embryonic stem cells were cultured following the protocols set forth above in Example 1.

(2) Imaging Conditions

The present examples used time-lapse fluorescence microscopic images. A cross-sectional image was acquired by focusing on the microscope lens. The cross-sectional images of each time frame (t=0, 1, 2, . . . ) were obtained by moving the focusing position as using a confocal microscopy. The 3D time-series images at certain time frame could be considered as constituting a volume data. Meanwhile, 2D time-series images could be time-lapse cross-sectional images at a constant cross-section or perspective images as using a wide-field microscope.

Figure 9:
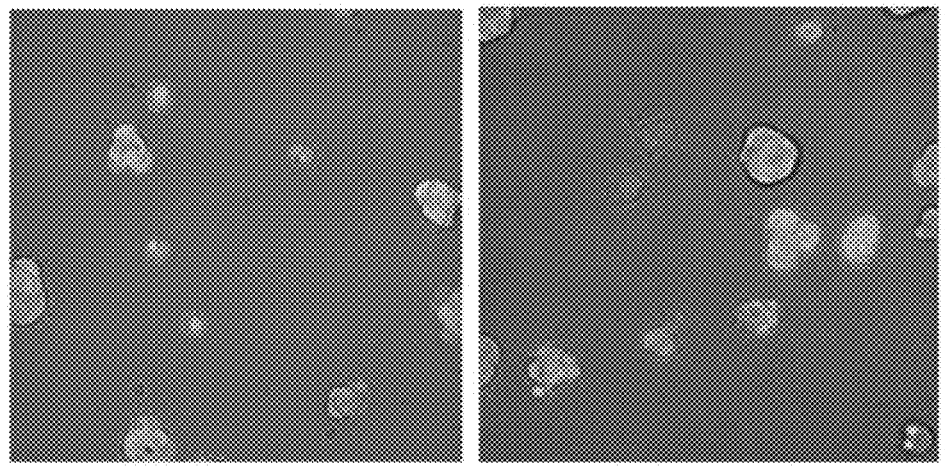
FIG. 9 provides fluorescence microscopic images of embryonic stem cell according to one working example of the present disclosure.

In this example, a set of 3D time-series images obtained from live Hela cells and a set of 2D time-series perspective images obtained from live mouse ES cells were studied. These data were captured at RIKEN BioResource center, Tsukuba, Japan. FIG. 9 shows two 2D fluorescence microscopic images, in which the mouse ES cells inside a cluster were observed by the labeling of the Venus (green) fluorescence protein and mRFP (monomeric red fluorescent protein).

(3) Image Processing

The images in this example were processed by our system implementing the method 200 described above. This system was developed using C/C++ programming and the Open Source Computer Vision (OpenCV) library. In addition, the Mathworks Matlab software was used for interface design. Through the present 2D and 3D user interface, states (moving, splitting, merging appearance and disappearance) and properties of detected cell clusters (quantitative measures such as centroids, positions, areas or volumes and growth rates) of the cell clusters could be observed.

The image of the left panel in FIG. 9 was processed by different methods to investigate the efficacy of the conventional methods in cell detection, compared with the present method 200.

The first conventional approach used was the frame differencing algorithm. In the frame differencing algorithm, two consecutive frames were defined as f(x,y,t−1) and d(x,y,t), respectively. Then, the frame differencing result was represented by the absolute differences between two adjacent frames, as defined in Equation 22 below:

$$FD(x,y,t)=|f(x,y,t)-f(x,y,t-1)| \qquad \text{(Equation 22)}.$$

The second conventional technique used was the background subtraction as defined in Equation 23 below:

$$\hat{f}(x,y,t)=|f(x,y,t)-B(x,y,t)| \qquad \text{(Equation 23)}.$$

Figure 10:
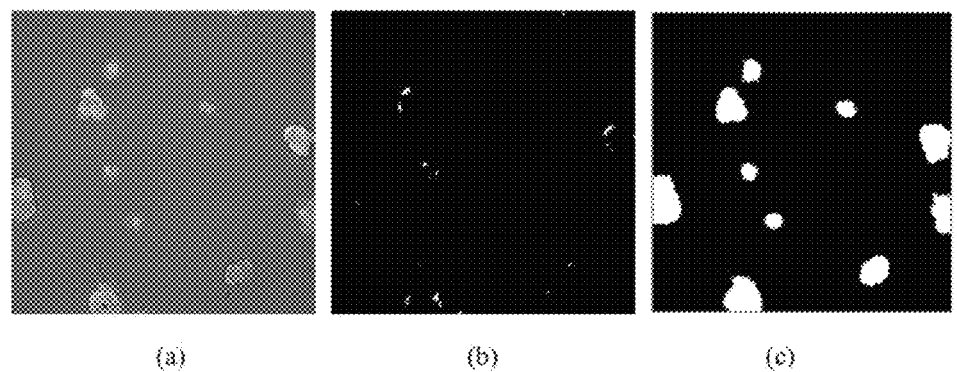
FIG. 10 is an example of the result of the cell cluster detection according to one working example of the present disclosure.

FIG. 10 shows an example of cell cluster detection, in which panel (a) is the original image, panels (b) is the result using the frame differencing algorithm, and panel (c) is the result using the background subtraction algorithm. By comparing the results presented in panels (b) and panel (c) of FIG. 10, it was observed that the frame differencing technique could not yield a satisfactory segmentation of cell clusters. On the other hand, although the conventional background subtraction algorithm gave a cell detection results better than the frame differencing algorithm, the fidelity of shapes of detected cells or cell clusters was somewhat lost due to the illumination changes in video sequences.

Figure 11:
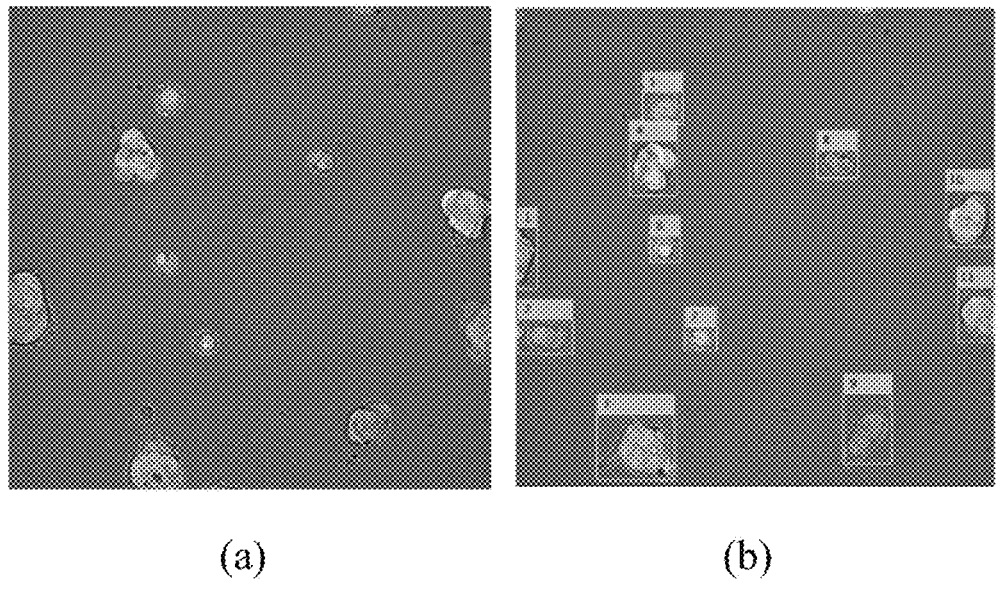
FIG. 11 is an example of the result of the cell clustering according to one working example of the present disclosure.

To address the deficiencies in the conventional methods, the adaptive background subtraction algorithm proposed in the present method 200 was applied to the same image in the cell detection step S201. FIG. 11 shows an example of the cell cluster detection by our method in which panel (a) is the original image, and panel (b) is the image processed using the adaptive background subtraction algorithm. As shown in the image of panel (b) of FIG. 11, each cell or cell cluster was given a unique label.

Figure 12:
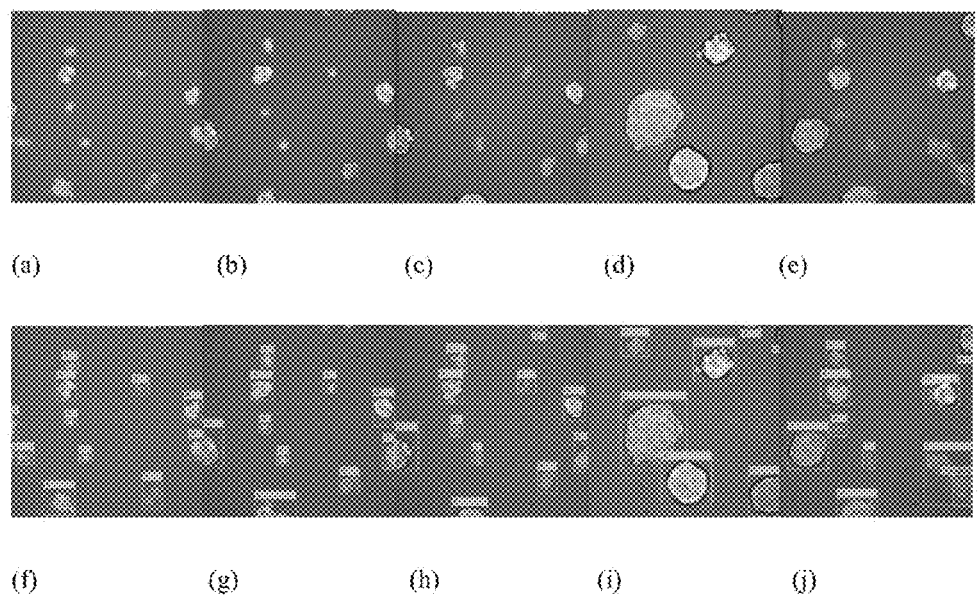
FIG. 12 is an example of the result of the cell cluster tracking according to one working example of the present disclosure.

The images, after being processed by steps S201 and S203 as described above, were subjected to the cell tracking step S205, in which the Discrete Kalman Filter was applied. FIG. 12 shows experimental tracking results of the cell cluster states (moving, appearance, disappearance or merging), wherein panels (a) to (e) show the original image sequence from the 2D (mouse ES cells) time-series images, whereas panels (f) to (j) are the corresponding tracking results. Panel (f) of FIG. 12 shows the detection results of the first frame in which each cluster center was assigned a unique label. In panel (g), FIG. 12, no clusters state change was observed; i.e., no cluster appeared, disappeared, merged and split; in this case, the present method 200. As could be seen in panel (h), FIG. 12, a new cluster appeared, whereas in panel (i), a cluster disappeared. It should be noted that since a cluster missing from the image may enter the image field again, the present method 200 only deleted a cluster label when the predicted center of such cluster was not found for several consecutive frames. Finally, in panel (j) of FIG. 12, it was observed that four clusters were merged into two clusters.

Figure 13:
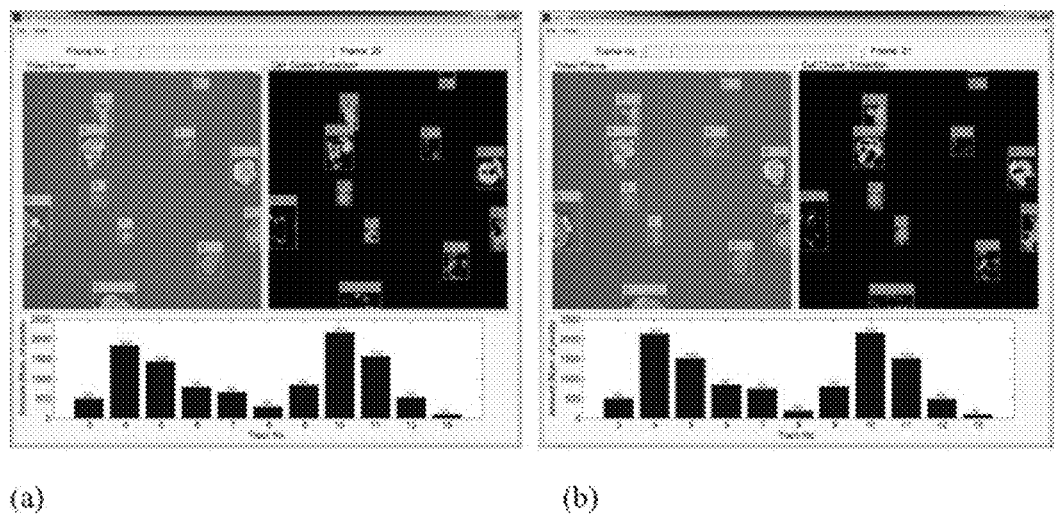
FIG. 13 presents a 2D interface for demonstrating states and properties of cell clusters in 2D time-series images.
Figure 14:
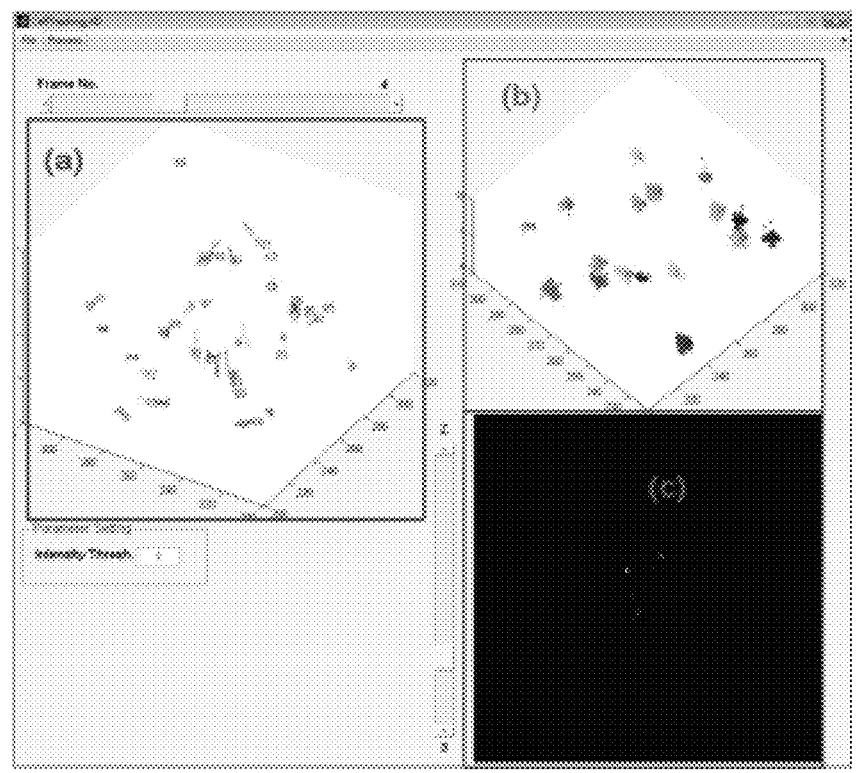
FIG. 14 presents a 3D interface for visualizing states and properties of cell clusters in 3D time-series images.

In the following, the implementation results for the 2D mouse ES cell time-series images and for the 3D Hela cell time-series images are shown in FIGS. 13 and 14, respectively.

As shown in FIG. 13, a 2D interface was provided to show the states of tracked cell clusters and the areas (pixel number in each cluster) at every frame in 2D time-series images. This interface provided a facile means so that the user may observe the state and area change of every cell cluster immediately. For example, the tenth cluster contained 2163 pixels and 2152 pixels at the 20$^{th}$ (panel (a)) and 21$^{st}$ (panel (b)) frame, respectively, and then, the growth rate (area change) of this cluster was calculated using the pixel numbers of neighboring frames.

The 3D interface as shown in FIG. 14 was provided to show the states and properties of detected cell clusters (quantitative measures such as centroids, positions, motions, areas and growth rates) at every frame in 3D time-series images. Referring to panel (a) of FIG. 13, the estimated 3D motion path of the centroid of each cell cluster was presented. Pane (b) of FIG. 13 shows the 3D shapes and states of the tracked cell clusters in one frame. This interface allowed the user to choose a suitable perspective for observing the shapes and states. Panel (c) of FIG. 13 shows the z-th slice of a set of 3D images in one frame.

In conclusion, the present method 200 is capable of processing cluster tracking much more efficiently (one frame in 1 second under similar frame sizes and cluster number) and obtaining accurate cluster positions and velocities. Using the proposed method, cell biologists can analyze a large amount of fluorescence microscopic images to investigate how different factors (such as, locations of cell clusters and culturing conditions) affect kinetics of cell cluster growth.

EXAMPLE 3

(1) Embryonic Stem (ES) Cell Formation

The mouse embryonic stem cells were cultured following the protocols set forth above in Example 1.

(2) Imaging Conditions

In this study, the CV-1000 (Yokogawa) confocal microscope was used to obtain fluorescence microscopic images of embryonic stem cells. The camera being used is the model Olympus UPLSApo60xO. Table 3 summarizes the microscope setting. Three channels of fluorescent microscopic images of embryonic stem cells were obtained simultaneously. Time-lapse confocal microscopy images were taken at a time interval of 20 minutes for a total of 24-hour duration, resulting in 144 image datasets, each set contained 9 slices of images with a thickness of 3.75 µm, and each slice image was with the resolution of 512×512 pixels and each pixel was approximately 0.26 µm.

TABLE 3

| Channel Name | Channel 1 | Channel 2 | Channel 3 |
| --- | --- | --- | --- |
| Excitation | 488 nm | 561 nm | Lamp |
| Power (%) | 10 | 30 | 19 |
| Emission | BP525/50 | BP617/73 | Through |
| Fluorescent | EGFP | mRFP | Bright field |
| Exposure | 15 ms | 15 ms | 15 ms |
| Gain | 60% | 40% | 20% |
| Binning | I | I | I |
| Z Slices | 9 | 9 | 9 |

Figure 15:
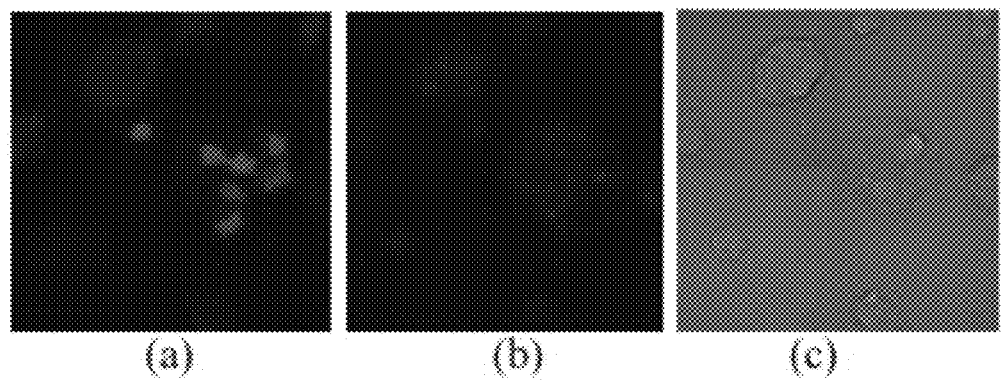
FIG. 15 is a fluorescence microscopic image of embryonic stem cell according to one working example of the present disclosure.

FIG. 15 shows representative fluorescence microscopic images of embryonic stem cells. Panel (a) of FIG. 15 is the image taken in Channel 1, which reveals the cytoplasmic labeling with the EGFP (green) fluorescence protein; panel (b) is taken in Channel 2, which reveals nuclei labeling by mRFP (monomeric red fluorescent protein); whereas panel (c) is the bright field (gray-level) image.

(3) Image Processing

The images in this example were processed by our system implementing the method 300 described above in connection with FIG. 2. This system was developed using C/C++ programming and the Open Source Computer Vision (OpenCV) library with Visual Studio 2012 as the integrated development environment. PC equipped with Intel® Core i7 CPU, 16G memory was used for software development and evaluation.

Figure 16:
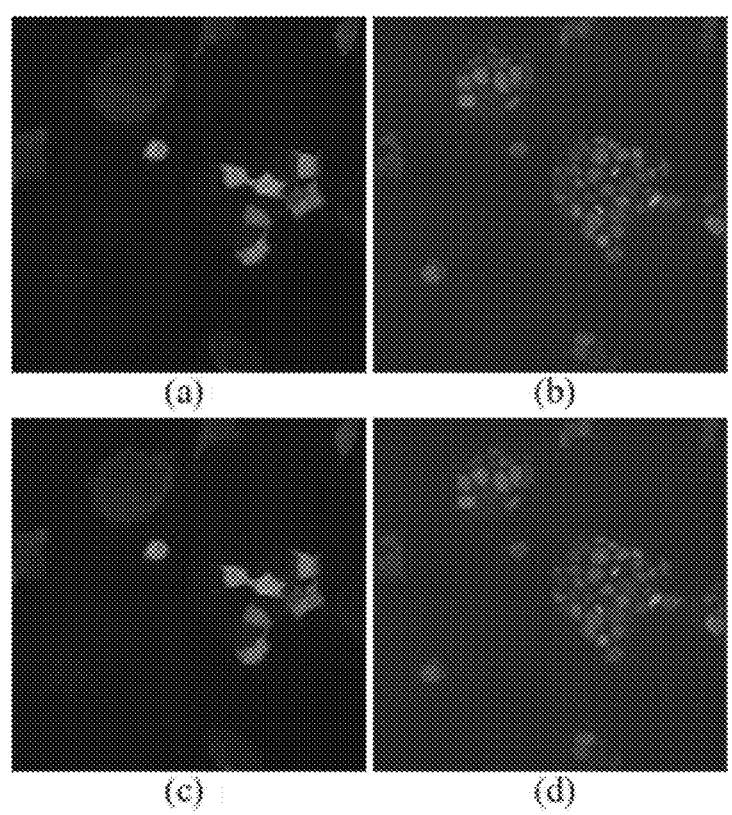
FIG. 16 is an example of the result of bilateral filtering for image enhancement according to one working example of the present disclosure.

In this example, the cytoplasm image (FIG. 16, panel (a)) and corresponding nucleus image (FIG. 16, panel (b)) were first processed by the bilateral filtering steps S301 and S311, respectively, and the results were shown in panels (c) and (d) of FIG. 16. As could be seen from FIG. 16, the bilateral filtering enhanced the boundaries of cytoplasm and nuclei while at the same time removed background noises of fluorescence microscopy images.

Figure 17:
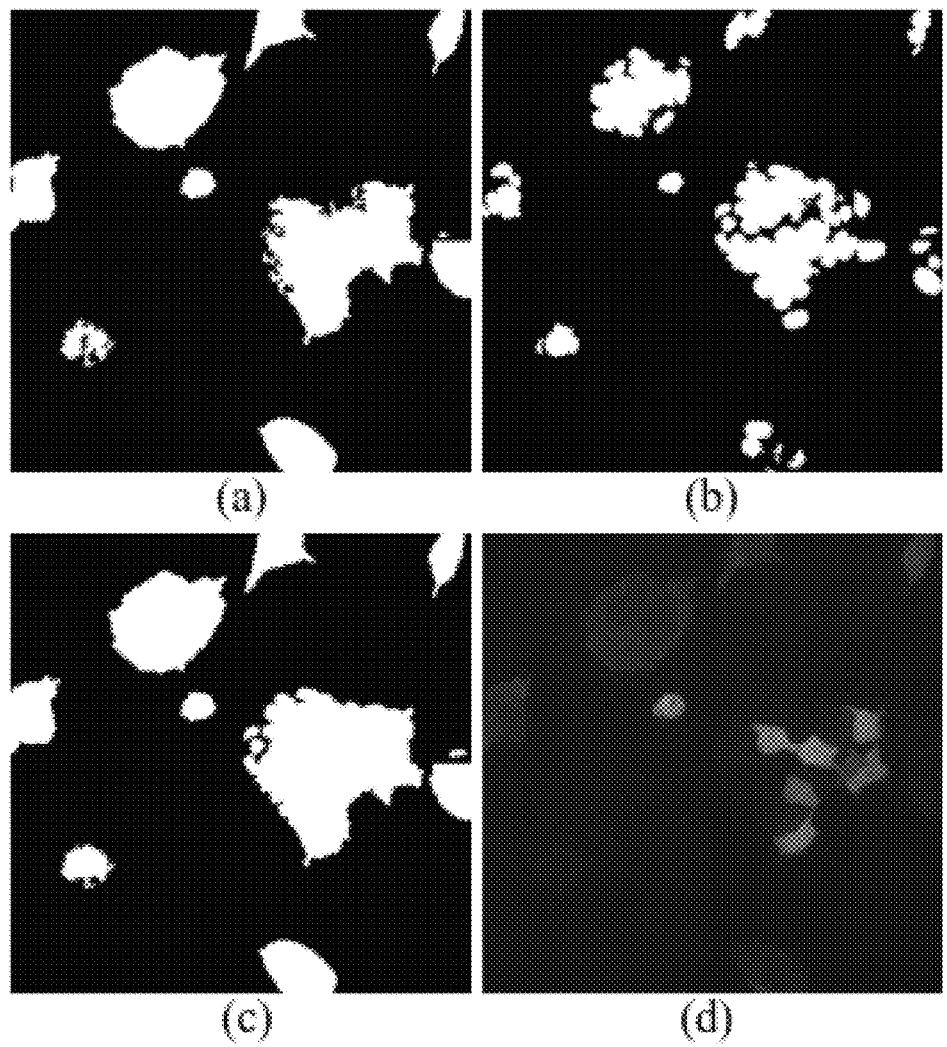
FIG. 17 is an example of the result after mesh-shift segmentation followed by OR operation according to one working example of the present disclosure.

Then, the cytoplasm image that had been processed by the bilateral filtering (see, FIG. 16, panel (c)) was subjected to the mean-shift segmentation step S303 and the contour refinement step S305. The representative images in FIG. 17 show the results of the cytoplasm image after the mean-shift segmentation (panel (a)); the nucleus image after the mean-shift segmentation (panel (b)); and the cytoplasm image after the contour refinement (panel (c)); panel (d) is the original cytoplasm image for comparison.

Figure 18:
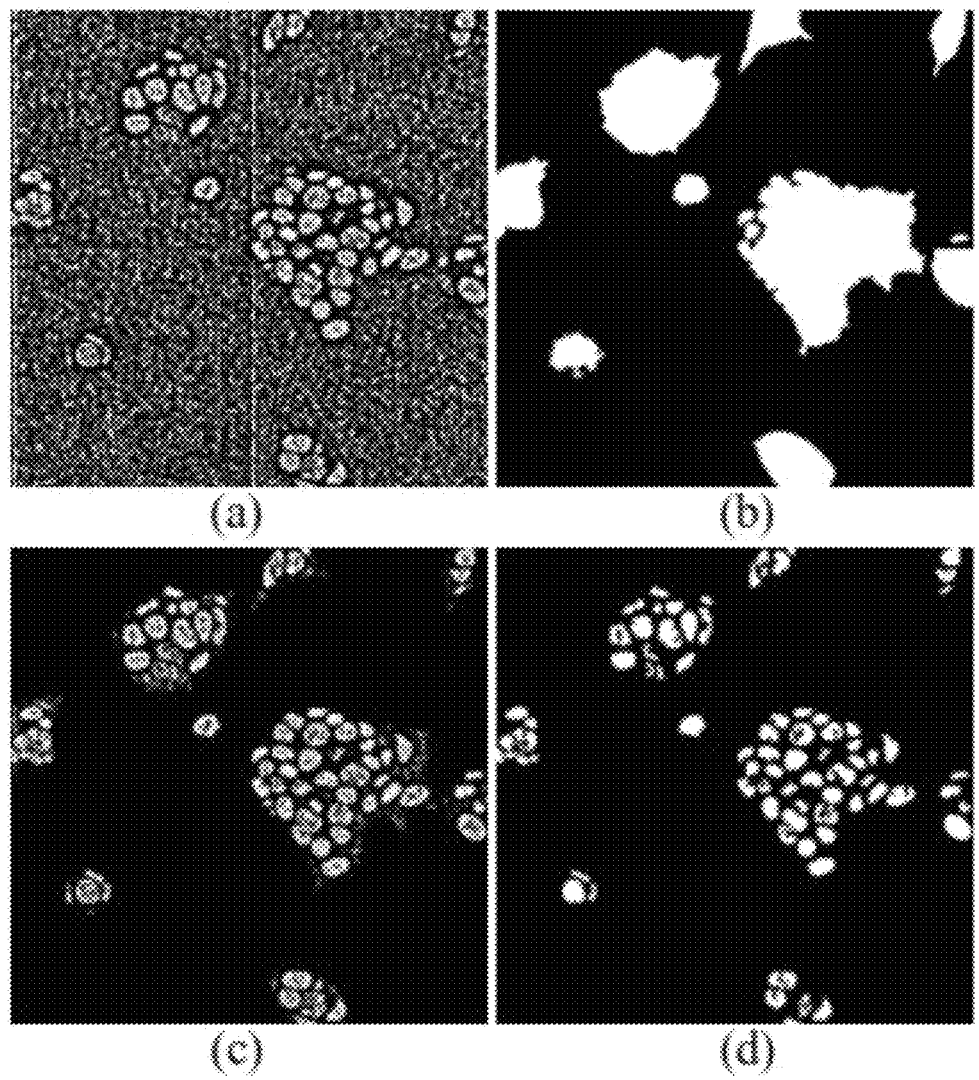
FIG. 18 is an example of the result after the adaptive thresholding and noise removal according to one working example of the present disclosure.

On the other hand, the nucleus image that had been processed by the bilateral filtering (see, FIG. 16, panel (d)) was subjected to the adaptive thresholding step S313 and the noise removal step S315. The representative images in FIG. 18 show the results of the nucleus image after the adaptive thresholding (panel (a)); the nucleus image in which the cytoplasm image after the contour refinement (i.e., FIG. 17, panel (c)) was used as a mask (panel (b)); the nucleus image after making (panel (c)); and the nucleus image after noise removal (panel (d)). As could be seen in FIG. 18, after the noise removal processes, the nucleus areas were well preserved, while irrelevant information such as image background noses were removed.

Figure 19:
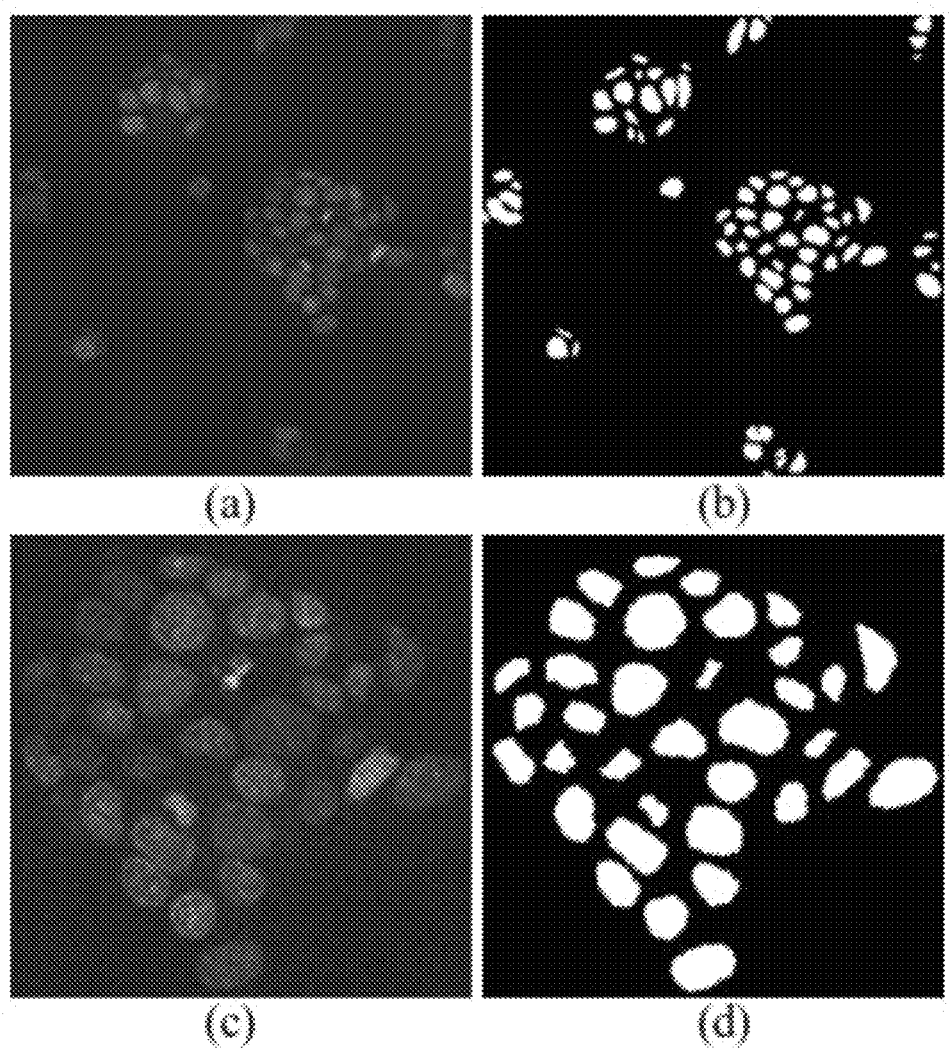
FIG. 19 is an example of the result after the watershed segmentation and contour refinement according to one working example of the present disclosure.

The nucleus image after the noise removal (i.e., FIG. 18, panel (d)) was then subjected to the watershed segmentation step S317. The results, as shown in FIG. 19, indicate that the after the watershed segmentation and contour refinement, each nucleus was extracted as a convex area without inside holes (panel (b)); panel (a) is the original image, whereas panels (c) and (d) are zoom-in images of the central colony from panels (a) and (b), respectively.

After every cytoplasm image and nucleus image was processed by the 2S cell detection step S310, these images were used for the subsequent 3D cell detection step S320, which employed the volume rendering method described above.

Figure 20:
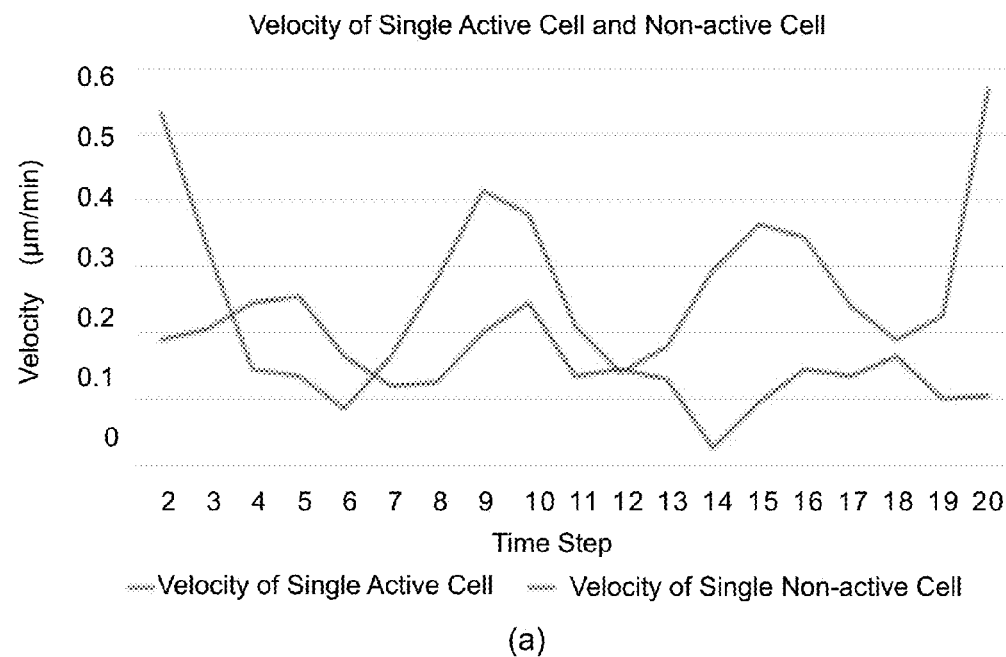
FIG. 20 is an example showing the comparison results of (a) the moving velocities and (b) the S/V ratios for the two mouse embryonic stem cells.
Figure 20:
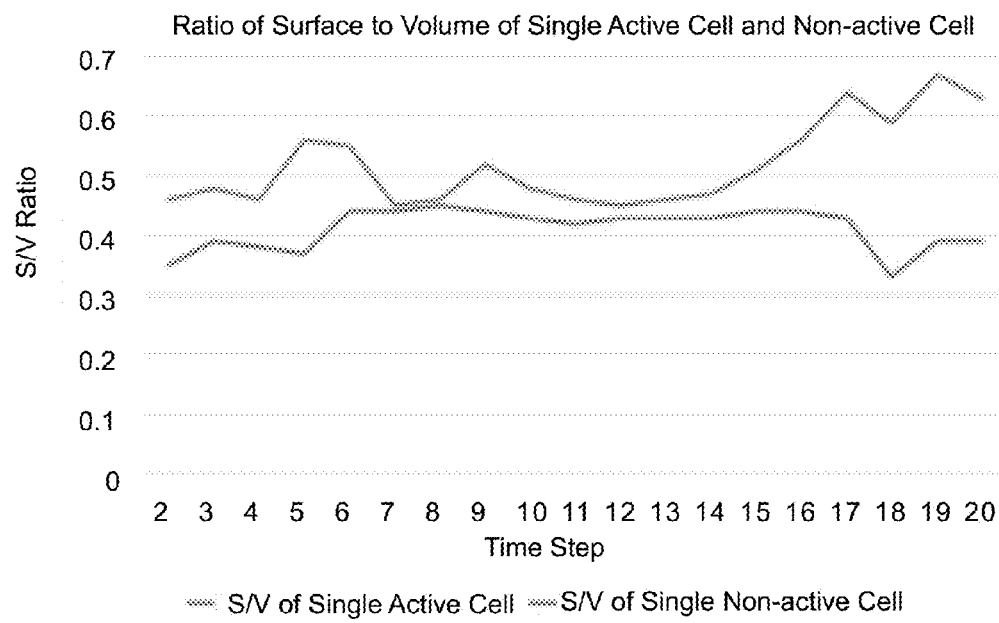

The thus generated Time-series 3D images were then used for quantitative analysis. For example, panel (a) and panel (b) of FIG. 20 are diagrams showing the velocities and the S/V ratios of two cells in time series. The data in FIG. 20 reveal that cells with a higher fluorescent response possessed both high velocity and high S/V ratio.

As could be appreciated, although various working examples are provided herein using embryonic stem cell cultures, the present disclosure is not limited thereto. Rather, as could be appreciated by persons having ordinary skill in the art, since the present methods and systems provide means for tracking and visualizing cells in a cell culture based on the shape and location of the nucleus, the present invention may be used to analyze cell kinematics of any cell, as long as it has a nucleus. For example, persons having ordinary skill in the art may readily apply the presently claimed methods and systems to other nucleated cells such as induced pluripotent stem (iPS) cells, somatic cells, and germ cells.

It will be understood that the above description of embodiments is given by way of example only and that various modifications may be made by those with ordinary skill in the art. The above specification, examples, and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. A method for analyzing cell kinematics in a nucleated cell culture from a time-series sequence of a plurality of fluorescence microscopic images of the nucleated cell culture, wherein each fluorescence microscopic image comprises a plurality of subimages taken from different fields, the method comprising the steps of,
   (a) identifying every cell nucleus in each fluorescence microscopic image;
   (b) identifying every cell cluster using the cell nuclei identified in the step (a); and
   (c) tracking the cells and/or cell clusters using the cell nuclei and cell clusters identified for the plurality of fluorescence microscopic images in steps (a) and (b) respectively, wherein
   the step (a) comprises the steps of,
   (a1) applying a bilateral filtering to each fluorescence microscopic image;
   (a2) adjusting the fluorescence illumination of the subimages of the fields across each fluorescence microscopic image that is processed by the step (a1);
   (a3) detecting every cell nucleus in each fluorescence microscopic image that is processed by the step (a2);
   (a4) refining the contour of the cell nucleus detected in the step (a3); and
   (a5) identifying voxels belonging to the same cell nucleus in each fluorescence microscopic image, wherein
       the step (a4) is performed by hole-filling followed by applying a convex hull algorithm.

2. The method of claim 1, wherein the step (a1) is performed by applying a non-linear filter according to Equation 1:

$$I_p = \frac{1}{W_p} \sum_{q \in S} G_{\sigma_s}(\|p - q\|) G_{\sigma_r}(|I_p - I_q|) I_q, \quad \text{(Equation 1)}$$

where p represents a target pixel in each fluorescence microscopic image, q represents a nearby pixel that is around the target pixel p, $I_p$ represents the color of the target pixel p, $I_q$ represents the color of the nearby pixel q, S represents a set of neighborhood pixels that are around the target pixel p, $G_{\sigma_s}$ represents the standard deviation of a Gaussian filter in which the pixel is weighted according to the distance between the target pixel p and the nearby pixel q, $G_{\sigma_r}$ represents the standard deviation of a Gaussian filter in which the pixel is weighted according to the pixel color differences between the target pixel p and the nearby pixel q, and $W_p$ is determined according to Equation 2:

$$W_p = \sum_{q \in S} G_{\sigma_s}(\|p - q\|) G_{\sigma_r}(|I_p - I_q|). \quad \text{(Equation 2)}$$

3. The method of claim 2, wherein the step (a2) is performed by applying adaptive thresholding according to Equation 3:

$$g(x, y) = \begin{cases} 255 & f_s(x, y) > t(x, y) \\ 0 & \text{otherwise} \end{cases}, \quad \text{(Equation 3)}$$

where g(x, y) represents the resulting image after the adaptive thresholding, $f_s(x,y)$ represents the resulting image after the step (a1), and t(x, y) is the adaptive threshold that is evaluated locally as the weighted average of the neighborhood pixels in each fluorescence microscopic image.

4. The method of claim 1, wherein the step (a5) is performed using 3D connected component labeling to identify a plurality of connected components.

5. The method of claim 4, further comprising the step of,
   (a6) assigning a unique identifier (ID) for the cell in the three-dimensional space.

6. The method of claim 1, wherein the step (b) is performed by hierarchical clustering.

7. The method of claim 1, wherein the step (b) comprises the step of assigning a unique identifier for the cell cluster.

8. The method of claim 4, wherein the step (b) comprises the steps of,
   (b1) determining the geometric centroid for one of the connected components as a cell center;
   (b2) counting the number n of nearby connected components that are within a radius r with respect to the cell center, and if n>k, then keeping the cell center; else, discarding the cell center;
   (b3) giving the remaining connected components a clustering label if they belong to the same cell cluster, wherein the clustering label is unique to the cell cluster;
   (b4) finding and drawing a bounding rectangle for the cell cluster; and
   (b5) returning the clustering label and bounding rectangle of the cell cluster.

9. The method of claim 8, wherein the step (c) comprises the steps of,
   (c1) generating a three-dimensional visualization of the cell cluster by polygonalizing the connected components and rendering the resultant polygons; and
   (c2) calculating the position and velocity of the cell cluster and each cell inside the cell cluster, and determining the state change of the cell cluster and the cells inside the cell cluster between frames.

10. The method of claim 9, wherein the step (c2) comprises the steps of,
    determining the geometric centroid for the cell cluster as a cluster center for the clustering label;
    calculating the number of the clustering labels for each frame;
    calculating the position p(x,y,z) of the cluster center for each frame;
    calculating the mean velocity v of the cluster center for each frame;
    if the number of the clustering labels at frame t+1 is less than the number of the clustering labels at frame t, then merging the clusters, else, keeping track of clusters; and
    returning the position and mean velocity of the cell cluster.

11. The method of claim 1, wherein the plurality of fluorescence microscopic images are time-lapse fluorescence microscopic images, and the step (a) is performed by adaptive background subtraction.

12. The method of claim 11, wherein the adaptive background subtraction is performed according to Equation 4:

$$\hat{f}(x,y,t) = |f(x,y,t) - B(x,y,t)| \quad \text{(Equation 4)},$$

where f(x,y,t) is the current frame and B(x,y,t) is the current background model; and if f̂(x,y,t)≥T, then (x,y,t)∈F, else, (x,y,t)∈B, where T is a pre-selected threshold, F represents the detected cell clusters, and B represents a background model without any cell clusters.

13. The method of claim 11, wherein the step (a) further comprises the steps of,
   (a1) labelling the regions of cell clusters in the frame, thereby assigning a cluster label for the cell cluster region; and
   (a2) using an inpainting method to produce a background model for subsequent frames, wherein the background model is according to Equation 5:

$$B(x, y, t) = \begin{cases} (1-\alpha) \cdot B(x, y, t-1) + \alpha \cdot f(x, y, t-1) & \text{if } (x, y, t-1) \in \mathcal{B} \\ I(x, y, t-1) & \text{if } (x, y, t-1) \in \mathcal{F} \end{cases}$$ (Equation 5)

where α is an updating factor in the range of 0 and 1, and I(x,y,t−1) is acquired using the inpainting method in the previous frame.

14. The method of claim 13, wherein the step (c) comprises the step of,
   (c1) determining the geometric centroid for the cell cluster as a cluster center.

15. The method of claim 14, wherein the step (c) further comprises the step of,
   (c2) applying a Discrete Kalman filter for the cluster in the frame according to Equation 6:

$$x_k = A\, x_{k-1} + B\, u_k + w_k$$

$$z_k = H_k x_k + v_k \quad \text{(Equation 6)},$$

where $X_{k-1}$ and $X_k$ represent the state vectors at time k−1 and k, respectively, the matrix A is a state transition matrix, the matrix B is a control-input matrix, $u_k$ is the control vector, $w_k$ is the process noise, $z_k$ is the measurement vector, $H_k$ is the observation transition model, and $v_k$ is the process noise, wherein $w_k$ has the Gaussian distribution with the covariance matrix $Q_k$ and $v_k$ has the Gaussian distribution with the covariance matrix $R_k$.

16. The method of claim 14, wherein the step (c) further comprises the steps of,
   (c3) tracking the cluster center of the cell cluster, wherein the plurality of fluorescence microscopic images are two-dimensional (2D) images or three-dimensional (3D) images, and the state vector $X_k$ is a 4-dimensional vector [x,y,dx/dt,dy/dt] for the 2D images or a 6-dimensional vector [x,y,z, dx/dt,dy/dt, dz/dt] for the 3D images, in which the x, y, z values represent the coordinates of the cluster center, the dx/dt, dy/dt, dz/dt values represent the moving velocity of the cluster center, and the transition matrix is according to Equation 7 for 2D images or Equation 8 for 3D images, $$A = \begin{bmatrix} 1 & 0 & 1 & 0 \\ 0 & 1 & 0 & 1 \\ 0 & 0 & 1 & 0 \\ 0 & 0 & 0 & 1 \end{bmatrix},$$ (Equation 7)

$$A = \begin{bmatrix} 1 & 0 & 0 & 1 & 0 & 0 \\ 0 & 1 & 0 & 0 & 1 & 0 \\ 0 & 0 & 1 & 0 & 0 & 1 \\ 0 & 0 & 0 & 1 & 0 & 0 \\ 0 & 0 & 0 & 0 & 1 & 0 \\ 0 & 0 & 0 & 0 & 0 & 1 \end{bmatrix}.$$ (Equation 8);

and (c4) updating the state of the cell cluster according to Equation 9 and Equation 10:

$$x_k = x_k^- + K_k(z_k^- - H_k^-)$$ (Equation 9), $$P_k = (1 - K_k H_k) P_k^-$$ (Equation 10), where $z_k$ is selected by the closest coordinate of the cell cluster, $P_k^-$ represents the error covariance, which is an a-prior estimate for the covariance at time k, and is obtained by Equation 11:

$$P_k^- = A P_{k-1} A^T + Q_{k-1}$$ (Equation 11), where $P_{k-1}$ represents the error covariance at time k−1 and $Q_{k-1}$ represents the covariance matrix of the process noise, $K_k$ is the Kalman gain and is obtained by Equation 12:

$$K_k = P_k^- H_k^T (H_k P_k^- H_k^T + R_k)^{-1}$$ (Equation 12).

17. The method of claim 14, wherein the step (c) further comprises the step of determining the state of the cell cluster at the next frame into one of the following states:
   (1) a moving state: if the cluster center of a predicted cell cluster is located inside the detected cell cluster region as defined by Equation 13, then assigning the previous cluster label to the detected cell cluster region:

if $x_k \in R_k^l$, then State=Moving (Equation 13), where $R_k^l$ represents the detected cell cluster region after the background subtraction in the k-th frame, where l=1 . . . n is the assigned label for the cell cluster region, and the location of the cell cluster is defined as $x_k^l$ with the cluster label l in the k-th frame;
   (2) an appearance state: if the detected cell cluster region is new and do not overlap with any existing cluster region as defined by Equation 14, then assigning a new cluster label to the detected cell cluster region and initializing a Discrete Kalman filter according to Equation 6:

if $R_k \cap R_{k-1}^l = \phi$, ∀l=1 . . . , $n_{k-1}$, then
       State=Appearance (Equation 14);

(3) a disappearance state: if the predicted cluster center is not located inside any existing cluster regions for consecutive k̂ frames as defined by Equation 15, then removing the cluster label of the predicted cluster:

if $x_{k-\hat{k}} \notin R_{k-\hat{k}}^l$, ∀l=1 . . . , $n_{k-\hat{k}}$, then
       State=Disappearance (Equation 15);

(4) a merging state: if two or more predicted cluster centers are located inside an existing cluster region as defined by Equation 16, then keeping the cluster label of the existing cluster region:

if $x_k \in R_k^l$ and $x_k \in R_k^{l'}$, $K \neq k'$, then State=Merging  (Equation 16);

(5) a splitting state: if a detected region is a new region that partially overlaps with any existing cluster regions as defined by Equation 17, then assigning a new cluster label to the detected region and initializing a Discrete Kalman filter according to Equation 6:

if $R_k^{l_1} \cap R_{k-1}^l \neq \phi$ and $R_k^{l_2} \cap R_{k-1}^l \neq \phi$, $l_1 \neq l_2$, then State=Splitting  (Equation 17).

18. The method of claim 1, wherein the plurality of fluorescence microscopic images comprise a plurality of cytoplasm images and a plurality of nucleus images, and each cytoplasm image has a corresponding nucleus image taken at the same time, and the step (a) comprises the steps of,
 (a1) applying a bilateral filtering to each cytoplasm image;
 (a2) adjusting the fluorescence illumination of the sub-images of the fields across each cytoplasm image processed by the step (a1) using a mean-shift segmentation method;
 (a3) applying the bilateral filtering to each nucleus image;
 (a4) refining the contour of each cytoplasm detected in the step (a2) using an OR operation between the cytoplasm image processed by the step (a2) with the corresponding nucleus image processed by the step (a3);
 (a5) adjusting the fluorescence illumination of the sub-images of the fields across each nucleus image processed by the step (a3) using an adaptive thresholding method;
 (a6) removing noise from the nucleus image processed by the step (a5) using the corresponding cytoplasm image processed by the step (a4) as a mask;
 (a7) labeling each nucleus area in the nucleus image processed by the step (a6) using a connected component labeling method;
 (a8) deleting small holes inside the nucleus area in the nucleus image processed by the step (a7) using a watershed segmentation method; and
 (a9) refining the contour of each nucleus in the nucleus image processed by the step (a8) using a convex hull method.

19. The method of claim 18, wherein the step (b) comprises the step of,
 (b1) identifying voxels belonging to the same cell nucleus in each nucleus image using 3D connected component labeling to identify a plurality of connected components;
 (b2) assigning a unique identifier (ID) for each cell in the three-dimensional space;
 (b3) determining the geometric centroid for one of the connected component as a cell center;
 (b4) counting the number n of nearby connected components that are within a radius r with respect to the cell center, and if $n \geq k$, then keeping the cell center; else, discarding the cell center;
 (b5) giving the remaining connected components a clustering label if they belong to the same cell cluster, wherein the clustering label is unique to each cell cluster;
 (b6) finding and drawing a bounding rectangle for the cell cluster; and
 (b7) returning the clustering label and bounding rectangle of the cell cluster.

20. The method of claim 19, wherein the step (c) comprises the step of,
 (c1) obtaining time-series 3D images of cell nuclei and cytoplasm by volume rendering the cytoplasm images and the nucleus images, wherein at each time step, two consecutive cytoplasm images and two consecutive corresponding nucleus images are rendered simultaneously.

21. The method of claim 20, wherein the step (c) further comprises the step of,
 (c2) determining the geometric centroid for the cell cluster or the nucleus as a 3D center; and
 (c3) calculating the velocity of the cell cluster or the nucleus based on the displacement between the 3D centers of adjacent time-steps.

22. The method of claim 19, further comprising the step of,
 (d) computing a ratio of the cytoplasm surface area to the volume (S/V ratio) of the cell.

23. A non-transitory computer-readable storage medium, encoded with computer-readable instructions for executing a method according to the claim 1.

24. A system for analyzing cell kinematics in a nucleated cell culture from a time-series sequence of a plurality of fluorescence microscopic images of the nucleated cell culture, comprising,
 an apparatus configured to obtain the plurality of fluorescence microscopic images;
 a control unit, comprising a processor and a memory for storing a plurality of instructions which, when executed by the processor, causing the processor to perform a method according to the claim 1.

* * * * *